US008623908B2

(12) United States Patent
Albeck et al.

(10) Patent No.: US 8,623,908 B2
(45) **Date of Patent: *Jan. 7, 2014**

(54) USE OF TELLURIUM COMPOUNDS FOR INHIBITION OF INTERLEUKIN-CONVERTING ENZYME

(75) Inventors: Michael Albeck, Ramat-Gan (IL); Benjamin Sredni, Kfar-Saba (IL)

(73) Assignee: Biomas Ltd., Jerusalem (IL)

( * ) Notice: Subject to any disclaimer, the term of this patent is extended or adjusted under 35 U.S.C. 154(b) by 36 days.

This patent is subject to a terminal disclaimer.

(21) Appl. No.: 12/728,362

(22) Filed: Mar. 22, 2010

(65) Prior Publication Data

US 2010/0233294 A1 Sep. 16, 2010

Related U.S. Application Data

(63) Continuation of application No. 11/663,032, filed as application No. PCT/IL2005/000990 on Sep. 15, 2005, now Pat. No. 7,709,524.

(60) Provisional application No. 60/610,660, filed on Sep. 17, 2004.

(51) Int. Cl.

*A61K 31/335* (2006.01)
*A61K 31/28* (2006.01)

(52) U.S. Cl.

USPC .......................................... 514/450; 514/492

(58) Field of Classification Search

USPC .................................................. 514/450, 492

See application file for complete search history.

(56) References Cited

U.S. PATENT DOCUMENTS

| | | | | |
|---|---|---|---|---|
| 3,369,550 | A | 2/1968 | Armao | |
| 4,752,614 | A | 6/1988 | Albeck et al. | |
| 4,761,490 | A | 8/1988 | Albeck et al. | |
| 4,764,461 | A | 8/1988 | Albeck et al. | |
| 4,929,739 | A | 5/1990 | Sredni et al. | |
| 4,962,207 | A | 10/1990 | Albeck et al. | |
| 5,093,135 | A | 3/1992 | Albeck et al. | |
| 5,102,908 | A | 4/1992 | Albeck et al. | |
| 5,213,899 | A | 5/1993 | Lucas | |
| 5,262,149 | A | 11/1993 | Sredni et al. | |
| 5,271,925 | A | 12/1993 | Sredni et al. | |
| 5,576,347 | A * | 11/1996 | Sredni et al. | 514/467 |
| 5,654,328 | A | 5/1997 | Sredni et al. | |
| 6,428,534 | B1 | 8/2002 | Joye et al. | |
| 6,472,381 | B1 * | 10/2002 | Albeck et al. | 514/162 |
| 6,552,089 | B1 | 4/2003 | Sredni et al. | |
| 6,747,008 | B1 | 6/2004 | Rogers et al. | |
| 7,629,382 | B2 * | 12/2009 | Sredni et al. | 514/467 |
| 7,709,524 | B2 * | 5/2010 | Albeck et al. | 514/450 |
| 2003/0148970 | A1 | 8/2003 | Besterman et al. | |
| 2006/0063750 | A1 | 3/2006 | Sredni et al. | |
| 2007/0298124 | A1 | 12/2007 | Albeck et al. | |
| 2008/0077024 | A1 | 3/2008 | Schnall | |
| 2008/0260770 | A1 | 10/2008 | Sredni et al. | |

FOREIGN PATENT DOCUMENTS

| | | | |
|---|---|---|---|
| DE | 4007473 | | 9/1991 |
| EP | 0583026 | | 2/1994 |
| GB | 1427415 | | 3/1976 |
| WO | 96/06618 | | 3/1996 |
| WO | 96/18392 | | 6/1996 |
| WO | 96/18401 | | 6/1996 |
| WO | 01/90070 | A2 | 11/2001 |
| WO | 01/94351 | A1 | 12/2001 |
| WO | 01/98325 | | 12/2001 |
| WO | 02/42278 | A2 | 5/2002 |
| WO | 02/094263 | A2 | 11/2002 |
| WO | 03/044038 | | 5/2003 |
| WO | 2004/002961 | A1 | 1/2004 |
| WO | 2004/058718 | A1 | 7/2004 |
| WO | 2005/060341 | | 7/2005 |
| WO | 2006/030437 | | 3/2006 |
| WO | 2006/030439 | | 3/2006 |
| WO | 2006/030440 | | 3/2006 |

OTHER PUBLICATIONS

Makarovsky et al., "Tellurium compound AS101 induces PC12 differentiation and rescues the neurons from apoptotic death", Annals of the New York Academy of Sciences, (2003), 1010 (Apoptosis), pp. 659-666.*

Montero et al., "AS-101: a modulator of in vitro T-cell proliferation". Anti-cancer Drugs, 4:351-354 (1993).

Kozenitzky et al., "Immunomodulatory effects of AS101 on interleukin-2 production and T-lymphocyte function of lymphocytes treated with psoralens and ultraviolet A" Photodermatol Photoimmunol Photomed 9:24-28 (1992).

Sredni et al., "The effect of the immunomodulator agent AS101 on interleukin-2 production in systemic lupus erythematosus (SLE) induced in mice by a pathogenic anti-DNA antibody". Clin. exp. Immunol. 79, 443-447 (1990).

Sredni et al., "The immunomodulator AS101 administered orally as a chemoprotective and radioprotective agent". Int J Immunopharmac., 14(4):613-619 (1992).

Nyska et al., "Toxicity study in rats of a tellurium based immunomodulating drug, AS-101: a potential drug for AIDS and cancer patients". Arch Toxicol, 63:386-393 (1989).

Kalechman et al., "Use and mechanism of action of AS101 in protecting bone marrow colony forming units-granulocyte-macrophage following purging with ASTA-Z 7557" Cancer Research 51:5614-5620(1991).

U.S. Appl. No. 60/610,660.

Blank et al., The effect of the immunomodulator agent AS101 on interleukin-2 production in systemic lupus erythematosus (SLE) induced in mice by a pathogenic anti-DNA antibody Clin. Exp. Immunol. 79, 443-447 (1990).

Xu et al., "The Cytoprotective Effect of the Immunomodulator AS101 Against Hydrochloride Induced Gastric Lesions" Res. Com Mol. Path. Pharm 87(1) 4-20 (1995).

(Continued)

*Primary Examiner* — Kevin E Weddington

(74) *Attorney, Agent, or Firm* — Browdy and Neimark, PLLC

(57) ABSTRACT

Use of tellurium-containing compounds for treating conditions in which inhibition of caspase-1/interleuFkin-1β enzyme (ICE) is beneficial is disclosed.

21 Claims, 8 Drawing Sheets

(56) References Cited

OTHER PUBLICATIONS

Kalechman et al., "Delay in the Onset of Systemic Lupus Erythematosus Following Treatment With the Immunomodulator AS101 Association With IL-10 Inhibition and Increase in TNF-alpha levels 1" J. Immunol. 159:2658-2667 (1997).
Kalechman et al., "Production of the Novel Mesangial Autocrine Growth Factors GDNF and IL-10 Is Regulated by the Immunomodulator AS 101" J. Am. Soc. Nephrol. 14:620-630 (2003).
Laurincová., "Interleukin-1 Family: From Genes to Human Disease" Acta. Univ. Palacki. Olomuc., Fac. Med. 143: 19-29 (2000).
Vonsover et al., "Inhibition of the Reverse Transcriptase Activity and Replication of Human Immunodeficiency Virus Type 1 by AS 101 in Vitro" AIDS Res Hum Retroviruses. 8(5):613-23 (1992).
Kim et al., "Regulation of Caspases by Nitric Oxide" Ann. N.Y. Acad. Sci. 962: 42-52 (2002).
Rathmell et al., "The Central Effectors of Cell Death in the Immune System" Ann. Rev. Immunol. 17: 781-828 (1999).
Ohta et al., "Expression of IL-18 in psoriasis" Arch. Dermatol. Res. 293: 334-342 (2001).
Yamamura et al., Interferon-g—Inducing Activity of Interleukin-18 in the Joint With Rheumatoid Arthritis Arthritis Rheum. 44: 275-285 (2001).
Kalechman et al., "Role of Endogenous Cytokines Secretion in Radioprotection Conferred by the Immunomodulator Ammonium Trichloro(dioxyethy1ene-0-0')tellurate" Blood 85: 1555 (1995).
Dinarello., "Biologic basis for interleukin-1 in disease" Blood 87: 2095-2147 (1996).
Kalechman et al., "Protective and Restorative Role of AS101 in Combination with Chemotherapy1" Cancer Res. 51: 1499-1503 (1991).
Sredni et al., Ammonium Trichloro(dioxoethylene-o,o1) tellurate (AS101) Sensitizes Tumors to Chemotherapy by Inhibiting the Tumor Interleukin 10 Autocrine LoopCancer Res. 64: 1843-1852 (2004).
Mendoza et al., Inhibition of Cytokine-Induced Microvascular Arrest of Tumor Cells by Recombinant Endostatin Prevents Experimental Hepatic Melanoma MetastasisCancer Res. 64: 304-310 (2004).
Yano et al., "Multifunctional interleukin-1β promotes metastasis of human lung cancer cells in SCID mice via enhanced expression of adhesion-, invasion- and angiogenesis-related molecules" Cancer Sci. 94: 244-252 (2003).
Strassmann et al., "The Immunomodulator AS-101 Inhibits IL-10 Release and Augments TNFa and 1L-1a Release by Mouse and Human Mononuclear Phagocytes" Cell Immunol. 176(2):180-5 (1997).
Hanna Rosenblatt-Bin et al., "The Immunomodulator AS101 Restores TH1 Type of Response Suppressed by Babesia rodhaini in BALB/c Mice" Cell. Immunol. 184: 12-25 (1998).
Buettner et al., "Activated STAT Signaling in Human Tumors Provides Novel Molecular Targets for Therapeutic Intervention1" Clin. Cancer Res. 8: 945-954 (2002).
Kalechman et al., "Effect of the immunomodulator AS101 on chemotherapy-induced multilineage myelosuppression, thrombocytopenia, and anemia in mice" Exp. Hematol. 23(13):1358-66 (1995).
Novick et al., "Interleukin-18 Binding Protein: A Novel Modulator of the Th1 Cytokine Response" Immunity 10: 127-136, (1999).
Tsutsui et al., "Pathophysiological roles of interleukin-18 in inflammatory liver diseases" Immunol. Rev. 174: 192-209, (2000).
Oppenheim et al., "There is more than one interleukin I" Immunol. Today 7: 45-56 (1986).
Sredni et al., "Cytokine secretion effected by synergism of the immunomodulator AS101 and the protein kinase C inducer bryostatin" Immunology 70(4):473-7 (1990).
Kalechman et al., "Synergistic Anti-Tumoral Effect of Paclitaxel (TAXOL)+AS101 In A Murine Model of B16 Melanoma: Association With RAS-Dependent Signal-Transduction Pathways" In. J. Cancer 86: 281-288 (2000).
Laichalk et al., "Tumor Necrosis Factor Mediates Lung Antibacterial Host Defense in Murine Klebsiella PneumoniaInfect" Immun. 64: 5211-5218 (1996).
Albeck et al., "Tellurium Compounds: Selective Inhibition of Cysteine Proteases and Model Reaction with Thiols" Inorg. Chem. 37: 1704-1712 (1998).
Giamila et al., "Interleukin-18 and interleukin-l[beta]: Two cytokine substrates for ICE (caspase-1)" J. Clin. Immunol. 19:1 (1999).
Fischer et al., "Interleukin-1 Receptor Blockade Improves Survival and Hemodynamic Performance in *Escherichia coli* Septic Shock, but Fails to Alter Host Responses to Sublethal Endotoxemia" J. Clin. Invest. 89: 1551-1557 (1992).
Singer et al., "Interleukin 1,8 Is Localized in the Cytoplasmic Ground Substance But Is Largely Absent From the Golgi Apparatus and Plasma Membranes of Stimulated Human Monocytes" J. Exp. Med. 167: 389-407 (1988).
Kalechman et al., "Radioprotective Effects of the Immunomodular AS1011" J. Immunol. 145: 1512-1517 (1990).
Echtenacher et al., "Requirement of Endogenous Recovery From Tumor Necrosis Factor/Cachectin for Experimental Peritonitis1" J. Immunol. 145: 3762-3766 (1990).
Finbloom et al., "IL-10 Induces the Tyrosine Phophorylation of tyk2 and Jakl Complexes in Human T Cells and Monocytes" J. Immunol. 155: 1079-1090 (1995).
Kalechman et al., "The Antitumoral Effect of the Immunomodulator AS101 and Paclitaxel (Taxol) in a Murine Model of Lung Adenocarcinoma" J. Immunol. 156: 1101-1109 (1996).
Esfandiari et al., "A Proinflammatory Role of IL-18 in the Development of Spontaneous Autoimmune Disease1" J. Immunol. 167: 5338-5347 (2001).
Kashiwamura et al., "Roles of Interleukin-18 in Tissue Destruction and Compensatory Reactions" J. Immunother. 25: S4-S11 (2002).
Sredni et al., Predominance of TH1 Response in Tumor-Bearing Mice and Cancer Patients Treated With AS 101J. Nat. Cancer Inst. 88: 1276-1284 (1996).
Tanaka et al., "Mature Form of Interleukin 18 Is Expressed in Rheumatoid Arthritis Synovial Tissue and Contributes to Interferon-y Production by Synovial T Cells" J. Rheumatol. 28: 1779-1787 (2001).
Sredni et al., "The Biological Activity and Immunotherapeutic Properties of AS-101, a Synthetic Organotellurium Compound" Nat. Immun. Cell Growth Regul. 7(3):163-8 (1988).
Shani et al., "Immunologic Effects of AS101 in the Treatment of Cancer Patients" Nat. Immun. Cell Growth Regul. 9 (3):182-90 (1990).
Sredni et al., " A New Immunomodulating compound (AS-101) with potential therapeutic application" Nature 330 (6144):173-6 (1987).
Tracey et al., "Anti-cachectin/TNF monoclonal antibodies prevent septic shock during lethal bacteraemia" Nature 330: 662-664 (1987).
Echtenacher et al., "Critical protective role of mast cells in a model of acute septic peritonitis" Nature 381: 75-77(1996).
Ghayur et al., "Caspase-1 processes IFN- 'Yinducing factor and regulates LPS-induced IFN-'Y production" Nature 386: 619-623 (1997).
Niu et al., "Constitutive Stat3 activity up-regulates VEGF expression and tumor angiogenesis" Oncogene 21: 2000-2008 (2002).
Wei et al., "Stat3 activation regulates the expression of vascular endothelial growth factor and human pancreatic cancer angiogenesis and metastasisOncogene" 22:319-329 (2003).
Repovic et al., "Oncostatin-M induction of vascular endothelial growth factor expression in astroglioma cells" Oncogene 22: 8117-8124 (2003).
Rosenblatt-Bin et al., "Antibabesial effect of the immunomodulator AS101 in mice: role of increased production of nitric oxide" Parasite Immunol. 18: 297-306 (1996).
Wong et al., "Elevation of plasma interleukin-18 concentration is correlated with disease activity in systemic lupus erythematosus" Rheumatol. 39: 1078-1081 (2000).
Gu et al., "Activation of Interferon-y Inducing Factor Mediated by Interleukin-1B Converting Enzyme" Science 275: 206-209 (1997).
Oberholzer et al., "Differential Effect of Caspase Inhibition on Proinflammatory Cytokine Release in Septic Patients" Shock 14: 253-258 (2000).

(56) References Cited

OTHER PUBLICATIONS

Villavicencio et al., "Induced Nitric Oxide Inhibits IL-6-Induced STAT3 Activation and Type II Acute Phase Mana Expression" Shock 13: 441-445 (2000).
Black et al. "Activation of Interleukin—1Beta by a Co-Induced Protease", FEBS Letters, 247(2): 386-390, 1989.
Hara et al. "Inhibition of Interleukin 113 Converting Enzyme Family Proteases Reduces Ischemic and Excitotoxic Neuronal Damage", Proc. Natl. Acad. Sci. USA, 94: 2007-2012 (1997).
Hardy "The Secret Life of the Hair Follicle", Trends in Genetics, 8(2): 41-78, 1992.
Kalechman et al. "Up-Regulation by Ammonium Trichloro(Dioxoethylene-0,0') Tellurate (AS 101) of Fas/Apo-1 Expression on B16 Melanoma Cells: Implications for the Antitumor Effects of AS101", The Journal of Immunology, 161:3536-3542, 1998.
Sredni et al. "Bone Marrow-Sparing and Prevention of Alopecia by AS101 in Non-Small-Cell Lung Cancer Patients Treated With Carboplatin and Etoside", Journal of Clinical Oncology, 13(9): 2342-2353, 1995.
Wieslander et al. "Antioxidative Properties ofOrganotellurium Compounds in Cell Systems", Biochemical Pharmacology, 55:573-584, 1998.
Siderowf et al. "Update on Parkinson Disease", Annals of Internal Medicine, 138(8): 651-658, 2003.
Sredni et al. "Hair Growth Induction by the Tellurium Immunomodulator AS 101: Association With Delayed Terminal Differentiation of follicular Keratinocytes and Ras-Dependent Up-Regulation of KGF Expression", The FASEB Journal, 18(2): 400-402,2004.
Makarovsky et al. "Tellurium Compound AS 10 I Induces PC 12 Differentiation and Rescue the Neurons From Apoptotic Death", Annals of the New York Academy of Sciences, 1010: 659-666,2003.
Kalechman et al. "Inhibition oflnt~rleukin-10 by the Immunomodulator AS101 Reduces Mesangial Cell Proliferation in Experimental Mesangioproliferative Glomerulonephritis", The Journal of Biological Chemistry, 279(23):24724-24732, 2004.
Kalechman et al. "Anti-IL-10 Therapeutic Strategy Using the Immunomodulator AS 101 in Protecting Mice From Sepsis-Induced Death: Dependence on Timing of Immunomodulating Intervention", the Journal of Immunology, 169 (1): 384-392, 2002.
Sredni et al. "The Protective Role of the Immunomodulator AS101 Against Chemotherapy-Induced Alopecia Studies on Human and Animal Models", International Journal ofCancer, 65(1): 97-103, 1996.
Sishi et al. "Defective Production of Interleukin-2 (IL-2) in Patients with Alopecia Areata", Chemical Abstracts, 108:519, 1988, Abstract.
Shohat et al. "In Vitro Cytokine Profile in Childhood Alopecia Areata and the Immunomodulatory Effects of AS-101 ", Clinical and Experimental Dematology, 30(4): 432-434, 2005.
Jimenez et al. "Interleukin I Protects From Cytosine Arabinoside-Induced Alopecia in the Rat Model", esearch Communications, the FASEB Journal, 5:2456-2458, 1991.
Gross et al. "Tellurium Dioxide Suspension in the Treatment of Seborrhea Capitis", A.M.A. Archives of Dermatology, 78(1 ): 92-94, 1958.
Shults "Treatments of Parkinson Disease. Circa 2003", Archives ofNeurology, 60: 1680-1684, Dec. 2003.
Merck "Human Immunodeficiency Virus (HIV) Infection", Merck Manual Home Edition for Patients and Caregivers, 10 P., May 19, 2008. http://merck.com/mmhe/sec 17 /ch 199/ch 199a.html.
Iupac "Acyl Groups", IUPAC Gold Book, 2 P., Nov. 27, 2007. http://goldbook.iupac.org/ A00 123 .html.
Dumont "The Interleukin-1 Families ofCytokines and Receptors: Therapeutic Potential for Immunomodulation and the Treatment of Inflammatory Disorders", Expert Opinion in Therapeutic Patents, 16(7): 879-912, 2006.
Delagarza "Pharmacologic Treatment of Alzheimer's Desease: An Update", American Family Physician, 68(7): 1365-1372, OJ Oct. 2003.
Boettner et al. "the Role of Rho GTPase in Disease Development", Gene, 286: 155-174, 2002.
Official Action Dated Aug. 26, 2008 From the Canadian Intellectual Property Office Re. Application No. 2,550,459.
Official Action Dated Feb. 14, 2007 From the US Patent and Trademark Office Re. U.S. Appl No. 11/226,374.
Official Action Dated Jan. 11, 2008 From the US Patent and Trademark Office Re. U.S. Appl. No. 11/226,374.
Official Action Dated Nov. 7, 2008 From the US Patent and Trademark Office Re. U.S. Appl. No. 11/226,374.
Office Action Dated 26 Jan. 2009 From the US Patent and Trademark Office Re. U.S. Appl. No. 11/663,031.
International Preliminary Report on Patentability Dated Mar. 29, 2007 From the International Bureau of WIPO Re. Application No. PCT/IL2005/000992.
International Preliminary Report on Patentability Dated Mar. 29, 2007 From the International Bureau of WIPO Re. application No. PCT/IL2005/000990.
International Prepliminary Report on Patentability Dated Mar. 29, 2007 From the International Bureau of WIPO Re. Application No. PCT/IL2005/000989.
International Preliminary Report on Patentability Dated Sep. 28, 2006 From the International Bureau of WIPO Re. Application No. PCT/IB2004/004163.
International Preliminary Report on Patentability Dated Apr. 26, 2007 From the International Bureau of WIPO Re. Application No. PCT/IL2005/000991.
Examination Report Dated Oct. 29, 2008 From the Government of India, Patent Office Re. Application No. 2606/CHENP/2006.
Communication Pursuant to Rules 109 and 110 EPC Dated Nov. 20, 2006 From the European Patent Office Re. Application No. 04801399.9.
Shults "Treatments of Parkinson Disease. Circa 2003", Archives of Neurology, 60: 1680-1684, Dec. 2003.
Merck "Human Immunodeficiency Virus (HIV) Infection", Merck Manual Home Edition for Patients and Caregivers, 10 P., May 19, 2008. http://merck.com/mmhe/sec 17/ch 199/ch 199a.html.
Dumont "The Interleukin-1 Families of Cytokines and Receptors: Therapeutic Potential for Immunomodulation and the Treatment of Inflammatory Disorders", Expert Opinion in Therapeutic Patents, 16(7): 879-912, 2006.
Delagarza "Pharmacologic Treatment of Alzheimer's Desease: An Update", American Family Physician, 68(7): 1365-1372,01 Oct. 2003.
Response Dated Apr. 7, 2009 to Official Action of Nov. 7, 2008 From the US Patent and Trademark Office Re: U.S. Appl. No. 11/226,374.
Official Action Dated Aug. 26, 2008 From the Canadian Intellectual Property Office Re.: Application No. 2,550,459.
Official Action Dated Jun. 18, 2009 From the US Patent and Trademark Office Re. U.S. Appl. No. 11/663,032.
Official Action Dated Feb. 14, 2007 From the US Patent and Trademark Office Re. U.S. Appl. No. 11/226,374.
Office Action Dated Jan. 26, 2009 From the US Patent and Trademark Office Re. U.S. Appl. No. 11/663,031.
Office Action Dated Jun. 5, 2008 From the Israeli Patent Office Re. Application No. 176333.
Examiner's Report Dated Apr. 15, 2009 From the Australian Government, IP Australia Re. Application No. 2004304716.
Examination Report Dated May 14, 2009 From the Intellectual Property Office of New Zealand Re. Application No. 554380.
Official Action Dated May 24, 2007 From the US Patent and Trademark Office Re. U.S. Appl. No. 11/226,374.

* cited by examiner

USE OF TELLURIUM COMPOUNDS FOR INHIBITION OF INTERLEUKIN-CONVERTING ENZYME

RELATED APPLICATIONS

This application is a continuation of U.S. patent application Ser. No. 11/663,032, filed on Mar. 16, 2007, which is a National Phase of PCT Patent Application No. PCT/IL2005/000990 having International Filing Date of Sep. 15, 2005, which claims the benefit of U.S. Provisional Patent Application No. 60/610,660 filed on Sep. 17, 2004. The contents of the above Applications are all incorporated herein by reference.

FIELD AND BACKGROUND OF THE INVENTION

The present invention relates to novel therapeutic methods and pharmaceutical compositions for treating conditions associated with inhibition of interleukin-converting enzyme (ICE).

Cytokines play an important role in a regulation of the immune system. Several studies indicate that variations in cytokine expression are associated with disease activity in immune mediated or inflammatory disorders, including autoimmune disorders (*Acta. Univ. Palacki. Olomuc., Fac. Med.* 143: 19-29, 2000; *Rheumatol.* 39: 1078, 2000; *J. Immunol.* 167: 5338, 2001), trauma (surgery) (*Blood* 87: 2095-2147, 1996), ischemic diseases (myocardial infarction) (*Acta. Univ. Palacki. Olomuc., Fac. Med.* 143: 19-29, 2000; *Cell. Immunol.* 184: 12, 1998), Alzheimer's disease (*Blood* 87: 2095-2147, 1996), liver diseases (*Immunol. Rev.* 174: 192-209, 2000), rheumatoid arthritis (*Arthritis Rheum.* 44: 275, 2001; *J. Rheumatol.* 28: 1779, 2001), obesity (*Shock* 14: 253, 2000), psoriasis (*Arch. Dermatol. Res.* 293: 334, 2001), and sepsis (*Acta. Univ. Palacki. Olomuc., Fac. Med.* 143: 19-29, 2000; *Blood* 87: 2095-2147, 1996; *Shock* 16: 441, 2000; *J. Med.* 31: 15, 2000).

The sepsis syndrome is an excessive, acute inflammatory response to a variety of noxious insults, particularly bacterial infection. The role of cytokines in the pathogenesis of sepsis is complex since both deficient and excessive immune responses have been associated with this syndrome. Pro-inflammatory cytokines are, on the one hand, required locally for effective anti-bacterial effector mechanisms (*J. Immunol.* 145: 3762, 1990; *Nature* 381: 75, 1996; *and Infect. Immun.* 64: 5211, 1996), but on the other hand they are potentially toxic when secreted into the circulation (*Nature* 330: 662, 1987; *J. Clin. Invest.* 89: 1551, 1992). Therefore, the ability to inhibit the production of highly active inflammatory mediators may have a beneficial effect in controlling the development of sepsis. Patients with septic shock who died had higher levels of IL-18 than patients who survived (*Shock* 14: 253, 2000).

IL-1β is crucial for the induction of fever and acute-phase response during local tissue damage; in systemic inflammation it contributes to inflammatory reaction (*Acta. Univ. Palacki. Olomuc., Fac. Med.* 143: 19-29, 2000). This cytokine is important in response to tissue damage and infection, but is not required for normal development and homeostasis. Serum levels of IL-1β and IL-1Ra are significantly elevated in severe sepsis (*Acta. Univ. Palacki. Olomuc., Fac. Med.* 143: 19-29, 2000).

The IL-1 family of cytokines, which include IL-18 and IL-1β, are key hormones of the immune system. Both IL-18 and IL-1β are expressed and produced by various types of cells from hematopoetic and nonhematopoetic lineages, such as dendritic cells, monocytes/macrophages, microglia cells, keratinocytes, intestinal epithelial cells, etc. Recent studies emphasize the pathophysiological role of IL-18 and IL-1β in a variety of neurodegenerative, autoimmune and inflammatory diseases, such as inflammation, hemaopoiesis and wound healing (*Immunol. Today* 7: 45-56, 1986).

Interleukin-18 is an early signal in the development of T-lymphocyte helper type 1 (Th1) responses. It acts together with IL-12 to induce various cytokines, including IFN-γ, to activate Th1 cells. IFN-γ is in turn responsible for inducing production of the soluble receptor protein, IL-18 binding protein (IL-18BP), a native down-regulator of IL-18 activity, which specifically binds IL-18 and neutralizes its biological activity in vitro and in vivo (*Immunity* 10: 127, 1999).

IL-18 and IL-1γ are expressed and produced in an inactive form, which requires activation by protease enzymes. The protease enzymes are divided into four families, (serine-, metallo-, aspartic- and cystein-proteases) based on their catalytic residues and mechanism of action. Whereas serine proteases utilize a nucleophilic hydroxyl of the serine residue and aspartic and metalloproteases posses carboxylates as active functionalities, the cysteine proteases have an active-site thiol-nucleophile.

The caspase enzymes (Cysteine Aspartic-Specific Proteases) are a family of intracellular cysteine endopepetidases, which cleave their substrates after aspartate residues (*Ann. Rev. Immunol.* 17: 781-828, 1999). The caspases are divided into two classes, based on the lengths of their N-terminal prodomains. Caspases-1,-2,-4,-5,-8, and -10 have long prodomains; and caspases-3,-6,-7, and -9 have short prodomains.

Caspase 1, which is also known and referred to herein, interchangeably, as interleukin-β-converting enzyme (ICE), is expressed as a proenzyme of 45 kD in many tissues (*J. Clin. Immunol.* 19:1, 1999). Upon stimulation, it undergoes activation by proteolytic cleavage. Active ICE is a tetramer of two non-identical subunits p10 and p20 in 2:2 proportion, which is uniquely responsible for cleaving pro-interleukin-113 (31 or 33 kD), into mature interleukin-1β (IL-1β)(17.5 kD), which consists of the C-terminal 153 residues of the inactive form; and pro-IL-18 (24 kD), which is cleaved at Asp35, into the biologically active 18 kD form (*J. Immunother.* 25: S4-S11, 2002; *Nature* 386: 619, 1997; *Science* 275: 206, 1997). The active cytokine is then released by a non-standard mechanism, since unlike the case with most secretory proteins, the precursor lacks a signal sequence and is not associated with membrane-bound compartments (*J. Exp. Med.* 167: 389-407, 1988).

ICE therefore plays an important role in physiological processes mediated by IL-1β and IL-18.

Various tellurium compounds have been described in the art as having immunomodulating properties. A particularly effective family of tellurium-containing compounds is taught, for example, in U.S. Pat. Nos. 4,752,614; 4,761,490; 4,764,461 and 4,929,739, whereby another effective family is taught, for example, in a recently filed U.S. Provisional Patent Application No. 60/610,660, which are all incorporated by reference as if fully set forth herein. The immunomodulating properties of this family of tellurium-containing compounds is described, for example, in U.S. Pat. Nos. 4,962,207, 5,093,135, 5,102,908 and 5,213,899, which are all incorporated by reference as if fully set forth herein.

One of the most promising compounds described in these patents is ammonium trichloro(dioxyethylene-O,O')tellurate, which is also referred to herein and in the art as AS101. AS101, as a representative example of the family of tellurium-containing compound discussed hereinabove, exhibits antiviral (*Nat. Immun. Cell Growth Regul.* 7(3):163-8, 1988; *AIDS Res Hum Retroviruses.* 8(5):613-23, 1992), and tumoricidal activity (*Nature* 330(6144):173-6, 1987; *J. Clin. Oncol.* 13(9):2342-53, 1995; *J. Immunol.* 161(7):3536-42, 1998).

It has been suggested that AS101, as well as other tellurium-containing immunomodulators, stimulate the innate and acquired arm of the immune response. For example, it has been shown that AS101 is a potent activator of interferon (IFN) in mice (*J. Natl. Cancer Inst.* 88(18):1276-84, 1996) and humans (*Nat. Immun. Cell Growth Regul.* 9(3):182-90, 1990; *Immunology* 70(4):473-7, 1990; *J. Natl. Cancer Inst.* 88(18):1276-84, 1996.)

It has also been demonstrated that AS101 induces the secretion of a spectrum of cytokines, such as IL-1, IL-6 and TNF-α, and that macrophages are one main target for AS101 (*Exp. Hematol.* 23(13):1358-66, 1995). AS101 was also found to inhibit IL-10 at the m-RNA level, which may cause an increase in IL-12 and IFN-γ (*Cell Immunol.* 176(2):180-5, 1997; *J. Natl. Cancer Inst.* 88(18):1276-84, 1996).

Other publications describing the immunomodulation properties of AS101 include, for example, "The immunomodulator AS101 restores T(H1) type of response suppressed by *Babesia rodhaini* in BALB/c mice". *Cell Immunol* 1998 February; "Predominance of TH1 response in tumor-bearing mice and cancer patients treated with AS101". *J Natl Cancer Inst* 1996 September; "AS-101: a modulator of in vitro T-cell proliferation". *Anticancer Drugs* 1993 June; "The immunomodulator AS101 administered orally as a chemoprotective and radioprotective agent". *Int J Immunopharmacol* 1992 May; "Inhibition of the reverse transcriptase activity and replication of human immunodeficiency virus type 1 by AS101 in vitro". *AIDS Res Hum Retroviruses* 1992 May; "Immunomodulatory effects of AS101 on interleukin-2 production and T-lymphocyte function of lymphocytes treated with psoralens and ultraviolet A". *Photodermatol Photoimmunol Photomed* 1992 February; "Use and mechanism of action of AS101 in protecting bone marrow colony forming units-granulocyte-macrophage following purging with ASTA-Z 7557". *Cancer Res* 1991 Oct. 15; "The effect of the immunomodulator agent AS101 on interleukin-2 production in systemic lupus erythematosus (SLE) induced in mice by a pathogenic anti-DNA antibody". *Clin Exp Immunol* 1990 March; "Toxicity study in rats of a tellurium based immunomodulating drug, AS-101: a potential drug for AIDS and cancer patients". *Arch Toxicol* 1989; "The biological activity and immunotherapeutic properties of AS-101, a synthetic organotellurium compound". *Nat Immun Cell Growth Regul* 1988; and "A new immunomodulating compound (AS-101) with potential therapeutic application". *Nature* 1987 Nov.

AS-101 has also been shown to have protective effects against lethal and sublethal effects of irradiation and chemotherapy (*Blood* 85: 1555, 1995; *J. Nat. Cancer Inst.* 88: 1276, 1996; *In. J. Cancer* 86: 281, 2000; *J. Immunol.* 156: 1101, 1996; *J. Immunol.* 145: 1507, 1990; *Cancer Res.* 51: 1499, 1991).

Moreover, AS101 can inhibit activity of STAT3 (Signal Transducer and Activator of Transcription 3) via IL-10 inhibition (*Cancer Res.* 64: 1843, 2004). When binding of IL-10 to the IL-10 receptor occurs, receptor-associated Janus activated kinase (Jak) tyrosin kinases are activated and stimulate downstream signaling. One of the main transcription factors being activated is STAT3. Activated, phosphorylated STAT3 is translocated to the nucleus and regulates specific gene expression (*J. Immunol.* 155: 1079, 1995). One of the target genes for STAT3 is vascular endothelial growth factor (VEGF) (*Clin. Cancer Res.* 8: 945, 2002; *Oncogene* 21: 2000, 2002; *Oncogene* 22: 319, 2003). This factor recently was found to be responsible for IL-18 induction (*Cancer Res.* 64: 304, 2004). Moreover, recently it was found that IL-1β alone (*Cancer Sci.* 94: 244, 2003) and together with oncostatin-M (*Oncogene* 22: 8117, 2003) induces up to sevenfold higher VEGF expression due to their mutual influence on STAT3. The ability of AS101 to down-regulate STAT3, may contribute to the overall inhibitory effect.

Furthermore, it was found that although AS101 shows no inhibition of serine, metallo, and aspartic proteases, it inhibits cysteine proteases, via a catalytic thiol oxidation (*Inorg. Chem.* 37: 1704-1712, 1998).

In addition to its immunomodulatory effect, AS101 is also characterized by low toxicity. Toxicity tests have shown that LD50 values in rats following intravenous and intramuscular administration of AS101 are 500-1000 folds higher than the immunologically effective dose.

Hence, while the prior art teaches various primary and secondary roles of tellurium-containing compounds such as AS101 as immunomodulators, it fails to teach the involvement of tellurium-containing compounds in inhibition of caspase-1/IL-1β-converting enzyme (ICE).

In view of the findings that a myriad of medical conditions is associated with ICE, there is a widely recognized need for and it would be highly advantageous to have, novel agents that are capable of inhibiting ICE and hence can be beneficially utilized in the treatment of such conditions.

SUMMARY OF THE INVENTION

The present invention teaches methods and pharmaceutical compositions for treating conditions associated with inhibition of interleukin-converting enzyme (ICE).

According to one aspect of the present invention there is provided a method of inhibiting interleukin-1β-converting enzyme in a subject in need thereof, the method comprising administering to the subject a therapeutically effective amount of at least one tellurium-containing compound.

According to another aspect of the present invention there is provided a method of treating a condition in which inhibition of interleukin-1β-converting enzyme is beneficial, the method comprising administering to a subject in need thereof a therapeutically effective amount of at least one tellurium-containing compound.

According to yet another aspect of the present invention there is provided a use of at least one tellurium-containing compound in the preparation of a medicament for treatment of a condition in which inhibition of interleukin-1β-converting enzyme is beneficial.

According to still another aspect of the present invention there is provided a pharmaceutical composition identified for use in the treatment of a condition in which inhibition of interleukin-1β-converting enzyme is beneficial, comprising at least one tellurium-containing compound and a pharmaceutically acceptable carrier.

According to further features in preferred embodiments of the invention described below, the pharmaceutical composition is packaged in a packaging material and identified in print, in or on said packaging material, for use in the treatment of conditions associated with inhibition of interleukin-converting enzyme The condition treatable by the methods or compositions of the present invention may comprise, for example, an IL-1 mediated disease, an inflammatory disease, an autoimmune disease, a destructive bone disorder, a proliferative disorder, an infectious disease, a degenerative disease, a disease associated with cell death, an excess dietary alcohol intake disease, retinal disorders, uveitis, inflammatory peritonitis, osteoarthritis, pancreatitis, asthma, adult respiratory distress syndrome, glomerulonephritis, rheumatoid arthritis, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs host disease, organ transplant rejection, organ apoptosis after burn injury, osteoporosis, leukemia's and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, septic shock, burns, Shigellosis, Alzheimer's disease, Huntington's disease, Kennedy's disease, prion disease, cerebral ischemia, epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, neurological damage due to stroke, ulcerative colitis, traumatic brain injury, spinal cord injury, hepatitis-B, hepatitis-C, hepatitis-G, yellow fever, dengue fever, or Japanese encephalitis, various forms of liver disease, renal disease, polycystic kidney disease, *H. pylori*-associated gastric and duodenal ulcer disease, HIV infection, tuberculosis, an immunotherapy for the treatment of various forms of cancer, organ failure, meningitis and a complication associated with coronary artery bypass grafts.

According to further features in preferred embodiments of the invention described below, the tellurium-containing compound of the present invention is a compound comprising at least one tellurium dioxide moiety and optionally and preferably is at least one of tellurium dioxide ($TeO_2$) per se, an organic complex of $TeO_2$ (as detailed hereinbelow), a compound having general Formula I:

Formula I

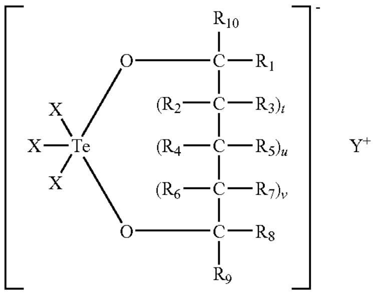

a compound having general Formula II:

Formula II

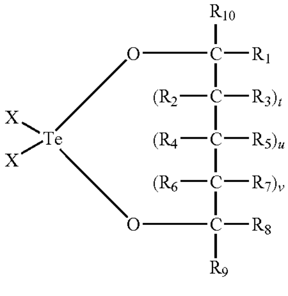

and a compound having general Formula III:

Formula III

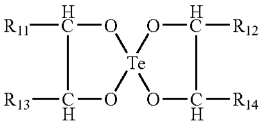

wherein:

each of t, u and v is independently 0 or 1;

each of m and n is independently an integer from 0 to 3;

Y is selected from the group consisting of ammonium, phsophonium, potassium, sodium and lithium;

X is a halogen atom; and each of $R_1$-$R_{14}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfonamido.

Preferably, the tellurium-containing compound has the general Formula I.

According to an embodiment in which the tellurium-containing compound has general Formula I, preferably t, u and v are each 0. More preferably, each of $R_1$, $R_8$, $R_9$ and $R_{10}$ is hydrogen; more preferably X is a halogen atom, most preferably the halogen atom is chloro. More preferably, Y is ammonium. The preferred compound according to this embodiment is referred to hereinafter as AS101.

According to still further features in the described preferred embodiments of the methods of the present invention, administration may be effected by a route selected from the group consisting of inhalation, oral, buccal, rectal, transmucosal, transdermal, intradermal, transnasal, intestinal and/or parenteral routes; intramuscular, subcutaneous and/or intramedullary injection routes; intrathecal, direct intraventricular, intravenous, intraperitoneal, intranasal, and/or intraocular injection routes; and/or direct injection into a tissue region.

Preferably, for systemic administration, a therapeutically effective amount of a compound of formula I, II or III ranges from about 0.01 $mg/m^2$/day to about 20 $mg/m^2$/day and, more preferably, from about 0.01 m $g/m^2$/day to about 10 $mg/m^2$/day.

According to still further features in the described preferred embodiments of the methods and uses of the present invention, the tellurium-containing compound forms a part of a pharmaceutical composition, further comprising a pharmaceutically acceptable carrier. Preferably, a concentration of tellurium-containing compound of formula I, II or III in the carrier ranges from about 0.01 weight percent to about 50 weight percents, more preferably from about 0.1 weight percent to about 25 weight percents, of the total weight of the composition. Optionally, the pharmaceutical composition may further comprise at least one additional active agent, including, but not limited to, an antineoplastic agent, an immunomodulator, an interferon and a non-steroidal anti-inflammatory drug (such as oxicams, piroxicam, isoxicam, tenoxicam, sudoxicam, CP-14,304, salicylates, aspirin, disalcid, benorylate, trilisate, safapryn, solprin, diflunisal, fendosal, acetic acid derivatives, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, fenamates, mefenamic, meclofenamic, flufenamic, niflumic, tolfenamic acids, propionic acid derivatives, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofen, pyrazoles, phenylbutazone, oxyphenbutazone, feprazone, azapropazone, trimethazone and derivatives, esters, salts and mixtures thereof).

According to still further features in the described preferred embodiments of the methods or compositions of the present invention, the composition may optionally further comprise at least one ingredient selected from the group consisting of a humectant, a deodorant agent, an antiperspirant, a sun screening agent, a sunless tanning agent, a pH adjusting agent, a chelating agent, a preservative, an emulsifier, an occlusive agent, an emollient, a thickener, a solubilizing agent, a penetration enhancer, an anti-irritant, a colorant, a propellant and a surfactant.

The pharmaceutical composition may be packaged in a packaging material and identified in print, in or on the packaging material, for use in treating a condition in which inhibition of interleukin-β-converting enzyme is beneficial.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the term "pharmaceutically acceptable" means approved by a regulatory agency of the Federal or a state government or listed in the U.S. Pharmacopeia or other generally recognized pharmacopeia for use in animals, and more particularly in humans. Herein, the phrases "physiologically suitable carrier" and "pharmaceutically acceptable carrier" are interchangeably used and refer to an approved carrier or a diluent that does not cause significant irritation to an organism and does not abrogate the biological activity and properties of the administered conjugate.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of methods and compositions comprising tellurium-containing compounds for inhibition of interleukin-β-converting enzyme (ICE).

The principles and operation of the compositions and methods according to the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As used herein, the phrase "tellurium-containing compound" encompasses any compound that includes one or more tellurium atoms and exhibits immunomodulating properties.

The phrase "immunomodulating properties" includes any effect of the compound on the immune response of a subject. Exemplary immunomodulating properties can be manifested, for example, by an effect on cytokines secretion, interleukins production, lymphocytes function, and the like.

While conceiving the present invention, it was postulated that since AS101 can interact with cysteine, affecting thiol oxidation, AS101, as well as other related tellurium-containing compounds may have an effect on ICE, and as a result on two known substrates of ICE, IL-18 and IL-1β.

Figure 1:
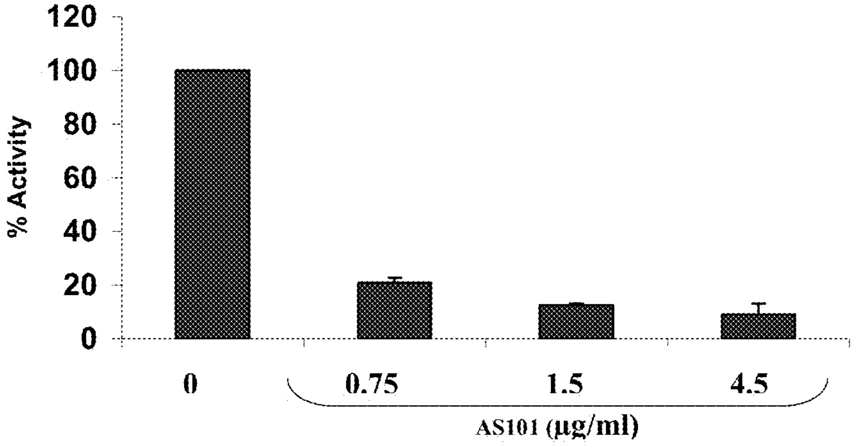
FIG. 1 is a bar graph demonstrating the effect of AS101 on ICE activity.
Figure 2:
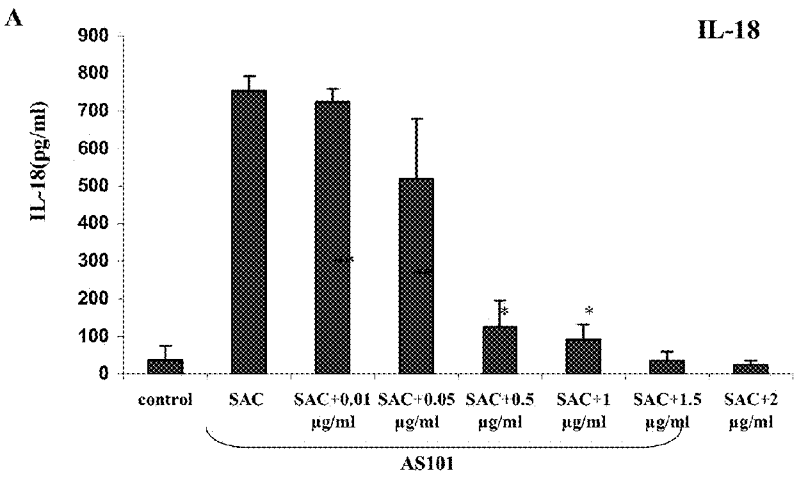
FIGS. 2*a-b* are bar graphs demonstrating the inhibitory effect of AS101 on secretion of IL-18 (FIG. 2*a*) and IL-1β (FIG. 2*b*)
Figure 2:
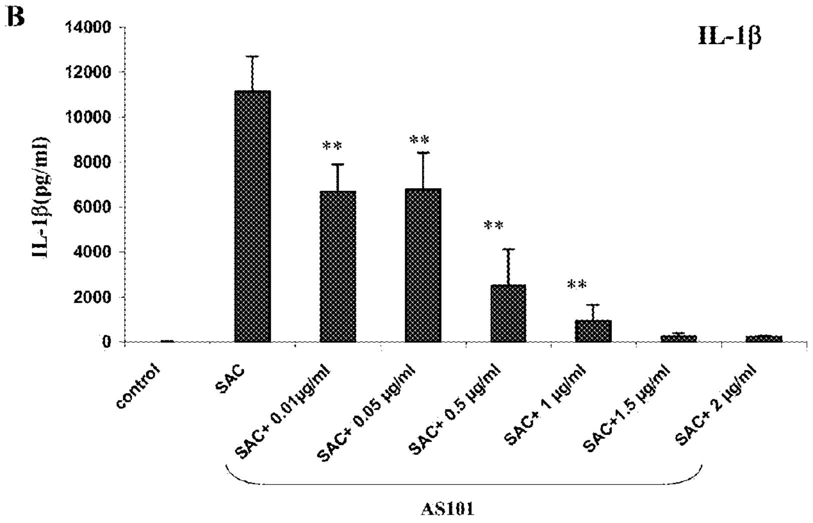
Figure 3:
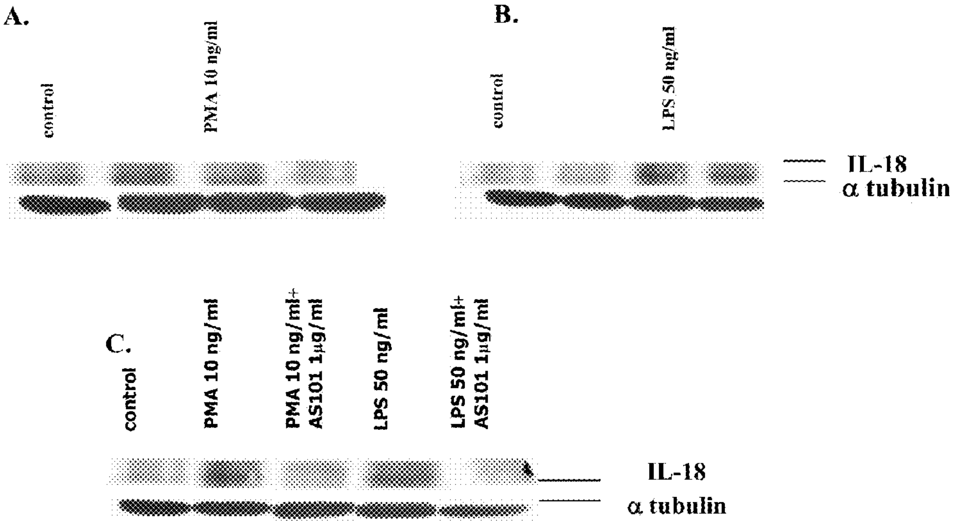
FIGS. 3*a-c* present Western Blot analysis of total cellular proteins from human HaCat keratinocytes using anti-IL-18 antibodies (FIGS. 3*a* and 3*b*) and the inhibitory effect of AS101 (FIG. 3*c*)

As shown in the Examples section below, while reducing the present invention to practice it was shown, using substrate specific enzymatic assay, that treatment of caspase-1 with AS101 inhibits enzymatic activity in a concentration dependent manner (FIG. 1). It was further shown that in freshly isolated human PBMC stimulated with *Staphylococcus aureus* Cowan strain, AS101 inhibits IL-18 as well as IL-1β secretion (FIG. 2). Moreover, it was shown that AS101 inhibits intracellular levels of mature IL-18 in stimulated human keratinocytes (FIG. 3).

In order to ensure that the inhibitory effect is mostly due to the direct caspase-1 inhibition at posttranslational level, IL-18 mRNA levels were examined. It was found that AS101 exerts no inhibitory effect at the IL-18 mRNA level (FIG. 4), indicating a post-transcriptional mechanism of action.

It was further demonstrated that the inhibitory effect of AS101 does not involves NO and IFN-γ, two possible down regulators of IL-18 production. Nitric Oxide (NO) has previously been shown to modulate cysteine proteases activity through S-nitrosylation of their active site cysteine (*Ann. N.Y. Acad. Sci.* 962: 42-52, 2002). AS101 has been found to be able to produce endogenous NO (*Parasite Immunol.* 18: 297, 1996*; Ann. N.Y. Acad. Sci.* 1010: 659, 2003). It was therefore postulated that the direct effect of AS101 on caspase-1 and the ability of AS101 to enhance NO levels might have a synergistic effect on caspase-1 inhibition.

In order to examine whether the elimination of NO will abrogate AS101 activity of IL-18 inhibition, the effect of L-NAME, nitric oxide synthase inhibitor was studied. It was surprisingly found, when used in PBMC, that the inhibitory effect of AS101 on IL-18 secretion was not diminished after using L-NAME.

IL-18 production has a self-regulating negative feedback loop. This cytokine can down regulate its own production by inducing the production of a native inhibitor, IL-18BP, through an IFN-γ dependent mechanism. Since AS101 has been previously shown to increase IFN-γ due to the direct inhibition of the anti-inflammatory cytokine, IL-1β, studies were carried out to determine whether the inhibitory effect of AS101 results from induction of IL-18BP directly and/or whether neutralization of IFN-γ would abrogate the inhibitory effect of AS101 on IL-18. It was found that AS101 treatment was not able to induce IL-18 production in human HaCat keratinocytes and neutralization of IFN-γ in PBMC does not abrogate IL-18 inhibition by AS101 (see, FIG. 6), implying that IFN-γ does not play a role in this inhibitory effect of AS101.

Organ injury observed in sepsis is due to the explosive release of cytokines into the plasma. Two of the known cytokines produced during this highly inflammatory reaction are IL-18 and IL-1β. The implications of AS101 inhibition of caspase-1 in vivo and the role of such inhibition in septic shock were therefore considered. In a model of sepsis, mice were treated with AS101 at various concentrations 2 hours following LPS injection. It was shown that AS101 down regulates IL-18 and IL-1β serum levels (see, FIG. 7) and increases survival (see FIG. 8).

At this relatively early point stage of inflammation, there is a rise of inflammatory response mediators, including TNF-α, IL-18, IL-1α, IL-1β, IFN-γ. It is therefore suggested that the immunomodulator, AS101, which known for its Th1 response induction via inhibition of IL-10, can also modulate the inflammatory response through a new mechanism of action.

On one hand, moderate inflammation can provide protection against invading pathogens, and it has been shown that AS101 can induce IFN-γ, IL-1α and other proinflammatory cytokines. On the other hand, AS101 is capable of attenuating and modulating this response by inhibiting the inflammatory products of ICE, IL-18 and IL-1β.

It is known that the family of cysteine proteases operates in a cascade mechanism, involving first initiators, then effectors. This mechanism of action is well known during apoptotic responses, but it has been found recently that ICE also requires "initiators", in particular, caspase-11 and -4, in order to become active (*Ann. Rev. Immunol.* 17: 781-828, 1999). Inhibition of IL-18 and IL-1β maturation in vitro and in vivo by AS101 may be due not only to its effect on caspase-1, but also partly due to its effect on other caspases which are required for the recruitment of ICE.

The data presented herein suggest that AS101, as well as related tellurium-containing compounds, may contribute a significant role in balancing the immune response in many pathophysiological conditions, via inhibition of the caspase-1 (ICE) enzyme.

The tellurium-containing compounds of the present invention are particularly useful in therapeutic applications relating to an IL-1β mediated disease, an inflammatory disease, an autoimmune disease, a destructive bone disorder, a proliferative disorder, an infectious disease, a degenerative disease, a disease associated with cell death, an excess dietary alcohol intake disease, retinal disorders, uveitis, inflammatory peritonitis, osteoarthritis, pancreatitis, asthma, adult respiratory distress syndrome, glomerulonephritis, rheumatoid arthritis, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs host disease, organ transplant rejection, organ apoptosis after burn injury, osteoporosis, leukemia's and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, septic shock, burns, Shigellosis, Alzheimer's disease, Huntington's disease, Kennedy's disease, prion disease, cerebral ischemia, epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, neurological damage due to stroke, ulcerative colitis, traumatic brain injury, spinal cord injury, hepatitis-B, hepatitis-C, hepatitis-G, yellow fever, dengue fever, or Japanese encephalitis, various forms of liver disease, renal disease, polycystic kidney disease, *H. pylori*-associated gastric and duodenal ulcer disease, HIV infection, tuberculosis, an immunotherapy for the treatment of various forms of cancer, organ failure, and meningitis. The compounds and compositions are also useful in treating complications associated with coronary artery bypass grafts.

Each of the tellurium-containing compounds utilized in the various aspects of the present invention preferably includes at least one tellurium dioxide moiety.

Thus, the compound can be, for example, an inorganic tellurium-containing compound such as, for example, tellurium dioxide ($TeO_2$) per se, halogenated tellurium, sulfonated tellurium, phsophorylated tellurium, as well as salts thereof (e.g., ammonium salts, alkaline salts, phosphonium salts and the like) and any complexes thereof.

The compound can alternatively be an organic tellurium-containing compound which includes one or more tellurium atoms and one or more organic moieties that are attached thereto.

Representative examples of inorganic tellurium-containing compounds that were shown to exert immunomodulating properties and hence are particularly useful in the context of the present invention include, for example, $TeO_2$ per se. Also included are compounds that form $TeO_2$ in aqueous solutions, preferably in the form of an organic complex such as, for example, a $TeO_2$ complex with citric acid or ethylene glycol. A representative example of the latter is the complex $TeO_2.HOCH_2CH_2OH.NH_4Cl$.

Organic tellurium-containing compounds that were shown to exert immunomodulating properties and hence are particularly useful in the context of the present invention include, for example, ammonium salts, or any other salts, of halogenated tellurium-containing compounds having a bidentate cyclic moiety attached to the tellurium atom. The bidentate cyclic moiety is preferably a di-oxo moiety having two oxygen atoms attached to the tellurium atom. Alternatively, the bidentate cyclic moiety can be a di-thio moiety, in which two sulfur atoms are attached to the tellurium atom.

Preferred compounds in this category are collectively represented by the general Formula I:

Formula I

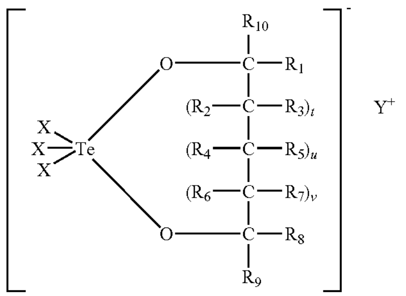

In the general Formula I above, each of t, u and v is independently 0 or 1, such that the compound may include a five-membered ring, a six-membered ring, or a seven-membered ring. Preferably, each of t, u and v is 0, such that the compound includes a five-membered ring.

X is a halogen atom, as described hereinabove, and is preferably chloro.

Y is selected from the group consisting of ammonium, phsophonium, potassium, sodium and lithium, and is preferably ammonium.

Each of $R_1$-$R_{10}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms. The alkyl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, sulfonamide, phosphonyl, phosphinyl, carbonyl, thiocarbonyl, carboxy, thiocarboxy, carbamate, thiocarbamate, amido, sulfonamido, and amino, as these terms are defined herein.

As used herein, the term "hydroxyalkyl" refers to an alkyl, as this term is defined herein, substituted by a hydroxy group, as defined herein, and includes, for example, hydroxymethyl, hydroxyethyl, hydroxypropyl and hydroxy-n-butyl.

As used herein, the term "halogen", which is also referred to herein interchangeably as "a halogen atom" or "halo", includes chloro (Cl), bromo (Br), iodo (I) and fluoro (F).

The term "haloalkyl" refers to an alkyl, as this term is defined herein, substituted by a halogen, as defined herein, and includes, for example, chloromethyl, 2-iodoethyl, 4-bromo-n-butyl, iodoethyl, 4-bromo-n-pentyl and the like.

The term "alkanoyloxy" refers to a carbonyl group, as define herein and includes, for example, acetyl, propionyl, butanoyl and the like.

The term "carboxyalkyl" refers to an alkyl, as this term is defined herein, substituted by a carboxy group, as defined herein, and includes, for example, carboxymethyl, carboxyethyl, ethylenecarboxy and the like.

The term "alkylcarbonylalkyl" refers to an alkyl, as this term is defined herein, substituted by a carbonyl group, as defined herein, and includes, for example, methanoylmethyl, ethanoylethyl and the like.

The term "amidoalkyl" refers to an alkyl, as this term is defined herein, substituted by an amide group, as defined herein, and includes, for example, $—CH_2CONH_2$; $—CH_2CH_2CONH_2$; $—CH_2CH_2CH_2CONH_2$ and the like.

The term "cyanoalkyl" refers to an alkyl, as this term is defined herein, substituted by an cyano group, as defined herein, and includes, for example, $—CH_2CN$; $—CH_2CH_2CN$; $—CH_2CH_2CH_2CN$ and the like.

The term "N-monoalkylamidoalkyl" refers to an alkyl, as this term is defined herein, substituted by an amide group, as defined herein, in which one of R' and R" is an alkyl, and includes, for example, —$CH_2CH_2CONHCH_3$, and —CH—$_2CONHCH_2CH_3$.

The term N,N-dialkylamidoalkyl refers to an alkyl, as this term is defined herein, substituted by an amide group, as defined herein, in which both R' and R" are alkyl, and includes, for example, —$CH_2CON(CH_3)_2$; $CH_2CH_2CON(CH_2$—$CH_3)_2$ and the like.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, phosphonyl, phosphinyl, carbonyl, thiocarbonyl, carboxy, thiocarboxy, carbamate, thiocarbamate, amido, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein. Representative examples are piperidine, piperazine, tetrahydro furane, tetrahydropyrane, morpholino and the like.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(═O)—R' group, where R' is hydrogen, alkyl, alkenyl, cycloalkyl, aryl, heteroaryl (bonded through a ring carbon) or heteroalicyclic (bonded through a ring carbon) as defined herein.

A "thiocarbonyl" group refers to a —C(═S)—R' group, where R' is as defined herein for R'.

A "carboxy" group refers to a —C(═O)—O—R' or a —O—C(═O)—R' group, where R' is as defined herein.

A "sulfinyl" group refers to an —S(═O)—R' group, where R' is as defined herein.

A "sulfonyl" group refers to an —$S(=O)_2$—R' group, where R' is as defined herein.

A "sulfate" group refers to a —O—$S(=O)_2$—OR' group, where R' is as defined herein.

A "sulfonamido" group refers to a —$S(=O)_2$—NR'R" group or a $R'S(=O)_2$—NR", with R' is as defined herein and R" is as defined for R'.

A "carbamyl" or "carbamate" group refers to an —OC(═O)—NR'R" group or a R"OC(═O)—NR'— group, where R' and R" are as defined herein.

A "thiocarbamyl" or "thiocarbamate" group refers to an —OC(═S)—NR'R" group or an R"OC(═S)NR'— group, where R' and R" are as defined herein.

An "amino" group refers to an —NR'R" group where R' and R" are as defined herein.

An "amido" group refers to a —C(═O)—NR'R" group or a R'C(═O)—NR" group, where R' and R" are as defined herein.

A "nitro" group refers to an —$NO_2$ group.

A "cyano" group refers to a —C≡N group.

The term "phosphonyl" describes a —O—P(═O)(OR')(OR") group, with R' and R" as defined hereinabove.

The term "phosphinyl" describes a —PR'R" group, with R' and R" as defined hereinabove.

As cited hereinabove, the compounds in this category are salts of organic tellurium-containing compounds. The salts can be, for example, ammonium salts, phsophonium salts and alkaline salts such as potassium salts, sodium salts, lithium salts and the like.

Hence, Y in Formula I above can be a phosphonium group, as defined herein, an ammonium group, as defined herein, potassium ($K^+$), sodium ($Na^+$) or lithium ($Li^+$).

As used herein, the term "phosphonium" describes a —$P^+R'R''R'''$ group, with R' and R" as defined herein and R''' is as defined for R'. The term "phsophonium", as used herein, further refers to a —$P^+R_6$ group, wherein each of the six R substituents is independently as defined herein for R, R'' and R'''.

The term "ammonium" describes a —$N^+R'R''R'''$ group, with R', R'' and R''' as defined herein.

More preferred compounds in this category include compounds having the general Formula I described above, in which Y is ammonium or phosphonium, t, u and v are each 0, and each of $R_1$, $R_8$, $R_9$ and $R_{10}$ is independently hydrogen or alkyl. These compounds can be represented by the following structure:

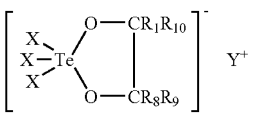

wherein each of $R_1$, $R_8$, $R_9$ and $R_{10}$ is independently hydrogen or alkyl, preferably methyl, and X is halogen, preferably chloro.

The presently most preferred compound for use in the context of the present invention has the following structure:

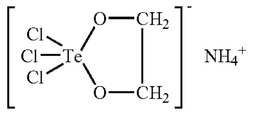

This compound is ammonium trichloro(dioxyethylene-O, O')tellurate, which is also referred to herein and in the art as AS101.

Additional representative examples of organic tellurium-containing compound that are suitable for use in the context of the present invention include halogenated tellurium having a bidentate cyclic moiety attached to the tellurium atom. The bidentate cyclic moiety is preferably a di-oxo ligand having two oxygen atoms attached to the tellurium atom. Alternatively, the bidentate cyclic moiety can be a di-thio ligand, in which two sulfur atoms are attached to the tellurium atom.

Preferred compounds in this category can be represented by the general Formula II:

Formula II

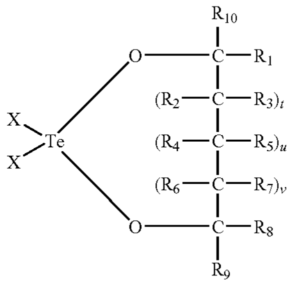

wherein t, u, v, X and $R_1$-$R_{10}$ are as defined hereinabove.

More preferred compounds are those in which t, u, and v are each 0, and X is chloro, such as, but not limited to, the compound having the following structure:

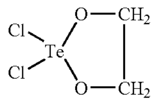

The above compound is also known as AS103.

The organic tellurium-containing compounds having Formulae I and II can be readily prepared by reacting tetrahalotelluride such as $TeCl_4$ with a dihydroxy compound, as is described in detail in U.S. Pat. Nos. 4,752,614, 4,761,490, 4,764,461 and 4,929,739, which are incorporated by reference as if fully set forth herein.

Additional representative examples of organic tellurium-containing compounds that are suitable for use in the context of the present invention include compounds in which two bidentate cyclic moieties are attached to the tellurium atom. Preferably, each of the cyclic moieties is a di-oxo moiety. Alternatively, one or more of the cyclic moieties is a di-thio moiety.

Preferred compounds in this category are collectively represented by the general Formula III:

Formula III

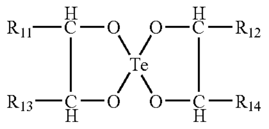

wherein each of $R_{11}$-$R_{14}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido, as these terms are defined herein.

The most preferred compound in this category is a compound in which each of $R_{11}$-$R_{14}$ is hydrogen. This compound is also known as AS102.

Additional organic tellurium-containing compounds that are suitable for use in the context of the present invention include those having the general Formula V:

Formula V

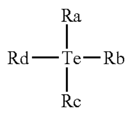

wherein each of Ra, Rb, Rc and Rd is independently selected from the group consisting of halogen alkyl, aryl, cycloalkyl, alkoxy, aryloxy, thioalkoxy, thioaryloxy, carboxy, carbonyl, thiocarboxy, thiocarbonyl, carbamyl, and thiocarbamyl, as these terms are defined hereinabove, whereby at least one of Ra-Rd is not halogen, namely, is selected from the group consisting of alkyl, aryl, cycloalkyl, alkoxy, aryloxy, thioalkoxy, thioaryloxy, carboxy, carbonyl, thiocarboxy, thiocarbonyl, carbamyl, and thiocarbamyl.

Compounds in this category include those in which one of Ra, Rb, Rc and Rd is halogen alkyl, aryl, cycloalkyl, alkoxy, aryloxy, thioalkoxy, thioaryloxy, carboxy, carbonyl, thiocarboxy, thiocarbonyl, carbamyl, or thiocarbamyl, whereby the others are halogen atoms, e.g., chloro.

Other compounds in this category include those in which two or three of Ra, Rb, Rc and Rd are as described above and the others are halogens e.g., chloro.

Other compounds in this category include those in which each of Ra, Rb, Rc and Rd is as described hereinabove.

The compounds described above can be administered or otherwise utilized in the various aspects of the present invention, either as is or as a pharmaceutically acceptable salt thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

The compounds described above can be administered to a subject suffering from an ICE-related condition, so as to treat the condition via ICE inhibition.

A representative list of ICE-related medical conditions that are treatable by the tellurium-containing compounds described herein, via an ICE inhibition mechanism, is presented hereinabove.

Suitable routes of administration may, for example, include the inhalation, oral, buccal, rectal, transmucosal, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes; and/or the route of direct injection into a tissue region of a subject of the present invention.

The term "therapeutically effective amount" or "pharmaceutically effective amount" denotes that dose of an active ingredient or a composition comprising the active ingredient that will provide the therapeutic effect for which the active ingredient is indicated. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

When administering systemically, a therapeutically effective amount of the tellurium-containing compounds described herein may range, for example, from about 0.01 $mg/m^2/day$ to about 20 $mg/m^2/day$ and thus can be for example, 0.01 $mg/m^2/day$, 0.02 $mg/m^2/day$, 0.03 $mg/m^2/day$, 0.04 $mg/m^2/day$, 0.05 $mg/m^2/day$, 0.1 $mg/m^2/day$, 0.5 $mg/m^2/day$, 1 $mg/m^2/day$, 2 $mg/m^2/day$, 3 $mg/m^2/day$, 4 $mg/m^2/day$, 5 $mg/m^2/day$, and up to 10 $mg/m^2/day$. Preferably, for systemic administration, a therapeutically effective amount of a compound of formula I, II or III ranges from about 0.01 $mg/m^2/day$ to about 10 $mg/m^2/day$. Higher therapeutically effective amounts, such as, for example, up to 20 $mg/m^2/day$ can also be employed.

Preferably, when administered intraperitoneally, the therapeutically effective amount is 0.01 $mg/m^2/day$ and higher and thus can be, for example, 0.01 $mg/m^2/day$, 0.05 $mg/m^2/day$, 0.1 $mg/m^2/day$, 0.2 $mg/m^2/day$, 0.5 $mg/m^2/day$, 0.6 $mg/m^2/day$, 0.7 $mg/m^2/day$, 0.8 $mg/m^2/day$, 0.9 $mg/m^2/day$, 1 $mg/m^2/day$, 2 $mg/m^2/day$, 3 $mg/m^2/day$, 4 $mg/m^2/day$, 5 $mg/m^2/day$, and up to 20.0 $mg/m^2/day$.

When administered orally in humans, a daily dose typically ranges between 0.1 mg and 200 mg, more preferably between 1 mg and 100 mg, depending on the age and weight of the subject. The total daily dose may be administered as a single dosage, or may be divided into a number of separate doses.

As used herein, the term "about" refers to ±10%.

The method according to this aspect of the present invention can further comprise, in addition to administering the tellurium-containing compounds described above, co-administration of an additional active agent. The co-administration can be effected prior to, concomitant with or subsequent to the administration of the tellurium-containing compound. The additional active agent is used for providing an additive beneficial effect in terms of the ailment being treated, conditions associated with the ailment being treated or other parameters such as psychological effects and prophylactic effects.

Hence, exemplary additional active agents according to this embodiment of present invention include, without limitation, one or more, or any combination of an antibiotic agent, an antimicrobial agent, an antibacterial agent, an antifungal agent, an antiviral agent, a steroidal anti-inflammatory agent, a non-steroidal anti-inflammatory agent, an anesthetic agent, an antipruriginous agent, an antiprotozoal agent, a suitable anti-oxidant, an antineoplastic agent, an immunomodulator an interferon, an antidepressant, an anti histamine, a vitamin, and a hormone.

Suitable antibiotics for use in this context of the present invention include, without limitation, benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate.

Representative examples of non-steroidal anti-inflammatory agents that are usable in this context of the present invention include, without limitation, oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Suitable antipruritic agents include, without limitation, pharmaceutically acceptable salts of methdilazine and trimeprazine.

Non-limiting examples of anesthetic drugs that are suitable for use in the context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

Suitable antimicrobial agents, including antibacterial, antifungal, antiprotozoal and antiviral agents, for use in the context of the present invention include, without limitation, beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, farnesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole and mixtures thereof.

Non-limiting examples of suitable anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of antineoplastic agents usable in the context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

Non-limiting examples of antidepressants usable in the context of the present invention include norepinephrine-reuptake inhibitors ("NRIs"), selective-serotonin-reuptake inhibitors (SSRIs), monoamine-oxidase inhibitors (MAOIs), serotonin-and-noradrenaline-reuptake inhibitors ("SNFIs), corticotropin-releasing factor (CRF) antagonists, α-adrenoreceptor antagonists, NK1-receptor antagonists, 5-$HT_{1A}$-receptor agonist, antagonists, and partial agonists and atypical antidepressants, as well as norepinephrine-reuptake inhibitors such as, but are not limited to amitriptyline, desmethylamitriptyline, clomipramine, doxepin, imipramine, imipramine-oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, tianeptine, and serotonin-reuptake inhibitors such as, but are not limited to, binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine.

Non-limiting examples of vitamins usable in the context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of dermatological active ingredients usable in the context of the present invention include jojoba oil and aromatic oils such as methyl salicylate, wintergreen, peppermint oil, bay oil, eucalyptus oil and citrus oils, as well as ammonium phenolsulfonate, bismuth subgallate, zinc phenolsulfonate and zinc salicylate. Non-limiting examples of antifungal agents include miconazole, clotrimazole, butoconazole, fenticonasole, tioconazole, terconazole, sulconazole, fluconazole, haloprogin, ketonazole, ketoconazole, oxinazole, econazole, itraconazole, terbinafine, nystatin and griseofulvin.

Non-limiting examples of antihistamines usable in the context of the present invention include chlorpheniramine, brompheniramine, dexchlorpheniramine, tripolidine, clemastine, diphenhydramine, promethazine, piperazines, piperidines, astemizole, loratadine and terfenadine.

Suitable hormones for use in the context of the present invention include, for example, androgenic compounds and progestin compounds.

Representative examples of androgenic compounds include, without limitation, methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing.

Representative examples of progestin compounds include, without limitation, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, fluorogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

In any of the different embodiments of the method of the present invention, the tellurium-containing compounds described herein can be provided to a subject either per se, or as part of a pharmaceutical composition where it is mixed with a pharmaceutically acceptable carrier.

Hence, according to another aspect of the present invention there is provided a pharmaceutical composition, which comprises a tellurium-containing compound as described herein and a pharmaceutically acceptable carrier.

Preferably, a concentration of tellurium-containing compound of formula I, II or III in the carrier ranges from about 0.01 weight percent to about 50 weight percents, more preferably from about 0.1 weight percents to about 25 weight percents, of the total weight of the composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to the subject treated.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered compound. As used herein, the term "carrier" refers to a diluent, adjuvant, excipient, or vehicle with which the therapeutic is administered.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer.

For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise glass, plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

The pharmaceutical composition described herein can alternatively be formulated in a form suitable for topical application on the treated area.

Hence, the compositions of the present invention can be, for example, in a form of a cream, an ointment, a paste, a gel, a lotion, a milk, a suspension, an aerosol, a spray, a foam, a shampoo, a hair conditioner, a serum, a swab, a pledget, a pad, a patch and a soap.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition.

Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions.

Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Thus, depending on the condition being treated and the composition form, the concentration of the tellurium-containing compound can be, for example, 0.01 weight percent, 0.05 weight percent, 0.1 weight percent, 0.5 weight percent, 1 weight percent, 2 weight percents, 3 weight percents, 4 weight percents or 5 weight percents. Preferably, the concentration of the tellurium-containing compound is 5 weight percents and higher and thus can be, for example, 5 weight percents, 6 weight percents, 7 weight percents, 8 weight percents, 9 weight percents or 10 weight percents. Concentrations higher than 10 weight percents can also be employed and thus, the concentration of the compounds can be, for example, 20 weight percents, 25 weight percents, 30 weight percents, 40 weight percents, 50 weight percents, 60 weight percents, 70 weight percents, 80 weight percents, and can be up to 85 weight percents of the total weight of the composition.

Each of the pharmaceutical compositions described herein may further comprise, according to an embodiment of the present invention an additional active agent, as described hereinabove.

Each of the pharmaceutical compositions described herein can optionally further comprise a variety of components that are suitable for providing the compositions with additional usage benefits. Such conventional optional components are well known to those skilled in the art and are referred to herein as "ingredients". Some non-limiting representative examples of these ingredients include humectants, deodorants, antiperspirants, sun screening agents, sunless tanning agents, hair conditioning agents, pH adjusting agents, chelating agents, preservatives, emulsifiers, occlusive agents, emollients, thickeners, solubilizing agents, penetration enhancers, anti-irritants, colorants, propellants and surfactants.

Thus, for example, the compositions of the present invention can comprise humectants or moisturizing agents. Representative examples of humectants that are usable in this context of the present invention include, without limitation, guanidine, glycolic acid and glycolate salts (e.g. ammonium slat and quaternary alkyl ammonium salt), aloe vera in any of its variety of forms (e.g., aloe vera gel), allantoin, urazole, polyhydroxy alcohols such as sorbitol, glycerol, hexanetriol, propylene glycol, butylene glycol, hexylene glycol and the like, polyethylene glycols, sugars and starches, sugar and starch derivatives (e.g., alkoxylated glucose), hyaluronic acid, lactamide monoethanolamine, acetamide monoethanolamine and any combination thereof.

The compositions of the present invention can further comprise a pH adjusting agent. The addition of a pH-adjusting agent is particularly preferred when the compositions are applied topically on the skin. The pH of these treated areas is typically lower than 6.0. Hence, it is preferable for the compositions of the present invention to have a pH value of between about 4 and about 7, preferably between about 4 and about 6, so as to avoid irritations to the skin or induction of imbalance of the bacteria population if the genital areas. Suitable pH adjusting agents include, for example, one or more of adipic acids, glycines, citric acids, calcium hydroxides, magnesium aluminometasilicates, buffers or any combinations thereof.

Representative examples of deodorant agents that are usable in the context of the present invention include, without limitation, quaternary ammonium compounds such as cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmlthyl sarcosine, lauroyl sarcosine, N-myristoyl glycine, potassium N-lauryl sarcosine, stearyl, trimethyl ammonium chloride, sodium aluminum chlorohydroxy lactate, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts, e.g. as the alkali metal carbonates and bicarbonates, ammonium and tetraalkylammonium carbonates and bicarbonates, especially the sodium and potassium salts, or any combination of the above.

Antiperspirant agents can be incorporated in the compositions of the present invention either in a solubilized or a particulate form and include, for example, aluminum or zirconium astringent salts or complexes.

The chelating agents are optionally added to the compositions of the present invention so as to enhance the preservative or preservative system. Preferred chelating agents are mild agents, such as, for example, ethylenediaminetetraacetic acid (EDTA), EDTA derivatives, or any combination thereof.

Suitable preservatives that can be used in the context of the present composition include, without limitation, one or more alkanols, disodium EDTA (ethylenediamine tetraacetate), EDTA salts, EDTA fatty acid conjugates, isothiazolinone, parabens such as methylparaben and propylparaben, propylene glycols, sorbates, urea derivatives such as diazolindinyl urea, or any combinations thereof.

Suitable emulsifiers that can be used in the context of the present invention include, for example, one or more sorbitans, alkoxylated fatty alcohols, alkylpolyglycosides, soaps, alkyl sulfates, monoalkyl and dialkyl phosphates, alkyl sulphonates, acyl isothionates, or any combinations thereof.

Suitable occlusive agents that can be used in the context of the present invention include, for example, petrolatum, mineral oil, beeswax, silicone oil, lanolin and oil-soluble lanolin derivatives, saturated and unsaturated fatty alcohols such as behenyl alcohol, hydrocarbons such as squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Suitable emollients, that can be used in the context of the present invention include, for example, dodecane, squalane, cholesterol, isohexadecane, isononyl isononanoate, PPG Ethers, petrolatum, lanolin, safflower oil, castor oil, coconut oil, cottonseed oil, palm kernel oil, palm oil, peanut oil, soybean oil, polyol carboxylic acid esters, derivatives thereof and mixtures thereof.

Suitable thickeners that can be used in the context of the present invention include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, fatty acids and their alkali salts and mixtures thereof.

Representative examples of solubilizing agents that are usable in this context of the present invention include, without limitation, complex-forming solubilizers such as citric acid, ethylenediamine-tetraacetate, sodium meta-phosphate, succinic acid, urea, cyclodextrin, polyvinylpyrrolidone, diethylammonium-ortho-benzoate, and micelle-forming solubilizers such as TWEENS and spans, e.g., TWEEN 80. Other solubilizers that are usable for the compositions of the present invention are, for example, polyoxyethylene sorbitan fatty acid ester, polyoxyethylene n-alkyl ethers, n-alkyl amine n-oxides, poloxamers, organic solvents, phospholipids and cyclodextrines.

Suitable penetration enhancers usable in context of the present invention include, but are not limited to, dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil. Such oils include, for example, safflower oil, cottonseed oil and corn oil.

Suitable anti-irritants that can be used in the context of the present invention include, for example, steroidal and non steroidal anti-inflammatory agents or other materials such as aloe vera, chamomile, alpha-bisabolol, cola nitida extract, green tea extract, tea tree oil, licoric extract, allantoin, caffeine or other xanthines, glycyrrhizic acid and its derivatives.

The compositions of the present invention may be packed or presented in any convenient way. For example, they may be packed in a tube, a bottle, or a pressurized container, using techniques well known to those skilled in the art and as set forth in reference works such as Remington's Pharmaceutical Science 15th Ed. It is preferred that the packaging is done in such a way so as to minimize contact of the unused compositions with the environment, in order to minimize contamination of the compositions before and after the container is opened.

The compositions are preferably identified in print, in or on the packaging material, for use in the treatment of ICE-related conditions.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Methods

Cell Culture:

Human peripheral blood mononuclear cells (PBMC) were isolated from randomly selected healthy donors by Ficoll-Hypaque (Pharmacia, Piscataway, N.J.) density-gradient centrifugation. PBMC were adjusted to $2.5\times10^6$ cells/ml and cultured in enriched RPMI 1640 medium (Biological industries, Kibbutz Beit Haemek, Israel) with 10% FCS (Biological industries) at 37° C. and 7% $CO_2$.

Human HaCat keratinocytes were adjusted to $1\times10^6$ cells/ml and cultured at 37° C. and 7% $CO_2$ in enriched Dulbecco's modified Eagle's medium (DMEM)(Biological industries, Kibbutz Beit Haemek, Israel), supplemented with 10% FCS (Biological industries).

Viability, as assessed by trypan blue exclusion method, was always found to be >95%.

Animals:

Male and female c57BL/6J and BALB/c 6-12 weeks of age mice were bred at Bar Ilan University from strains obtained from Harlan Laboratories, Israel. Animal experiments were performed in accordance with approved institutional protocols and approved by the Institutional Animal Care and Use Committee.

Reagents:

The following bacterial antigens, antibodies and peptides were applied: heat-inactivated *Staphylococcus aureus* Cowan strain (SAC ($10^{-3}$ v/v; Calbiochem, Bad Homburg, Germany), Lipopolysaccharide [LPS (40-60 ng/ml, in vitro) and (0.5 mg/mouse, in vivo); *Salmonella Enteritidis*, Sigma Aldrich, Rehovot, Israel), Phorbol-12-Myristate-13-Acetate (PMA (5-15 ng/ml); Sigma Aldrich, Rehovot, Israel), anti-human IFN-γ-neutralizing IgG (0.1 μg/ml; R&D Systems, Minneapolis, Minn.), NOS inhibitor, L-nitroarginine-methyl-ester (L-NAME), and it's inactive analog, D-nitroarginine-methyl-ester (D-NAME) (20 nM; Sigma, Munich, Germany). rCaspase-1 and specific inhibitor (Ac-YVAD-CHO) (Biomol International Industries L.P. Canada). Caspase-1 colorimetric substrate (Ac-YVAD-pNA)(Alexis Biochemicals, Inc. San Diego, Calif.).

AS101 was supplied by M. Albeck from the chemistry department at Bar Ilan University, in a solution of PBS, pH 7.4, and maintained at 4° C.

Induction of Cytokine Secretion In vitro and In vivo:

In vitro Assays:

Cells were first treated with various concentrations of AS101 and after 1 hour SAC was added. After 24 hours, supernatants were collected and evaluated for cytokine content. Viability at the end of these experiments, as assessed by tryptan blue exclusion method, was always found to be >95%.

In vivo Assays:

For serum cytokine evaluation, PBS or AS101 was injected intraperitoneally (i.p.) 2 hours following LPS treatment. For survival experiments AS101 was injected i.p. daily at various concentrations starting 1 hour and up to 24 hours following LPS until the end of the experiment.

Quantification of Cytokine Levels:

The R&D Systems (Minneapolis, Minn.) IL-18 and IL-1β ELISA kits were used for the quantitative measurement of these cytokines either in supernatants or in mice sera.

Caspase-1 Activity Enzymatic Assay:

DTT, which is present in the commercial enzyme solution, interacts with AS101 and thus would interfere with the inhibition studies. Therefore removal of DTT from the enzyme solution prior to the enzymatic assay was necessary. Gel permeation chromatography was carried out at 4° C. 50 μl solution of commercial activated rCaspase-1 was loaded on a 1×15 cm Sephadex G-15 column (Pharmacia), preequilibrated with assay buffer containing: 50 mM Hepes, 100 mM NaCl, 0.1% CHAPS, 1 mM EDTA, 10% Glycerol at pH 7.4. The enzyme was eluted with the same buffer (degassed) at 0.5 ml/minute and 500 μl fractions were collected. The enzyme-substrate reaction was measured continuously with 1 min. intervals for a total time of 1 hour at 30° C. and was read at 405 nm. The total volume of the reaction was 100 μl and contained as following: 50 μl rCaspase-1 (0.8 U/μl), 25 μl colorimetric substrate (Ac-YVAD-pNA, 200 μM), 25 μl of AS101 at various concentrations (2.5 μM, 5 μM, 10 μM) in assay buffer.

Western Blot Analysis:

Total cell extracts were prepared by suspension in ice-cold lysis buffer containing 50 mM Tris (pH 8.0), 150 mM NaCl, 1% NP-40, 0.1% SDS, 5 mM EDTA, 0.2 mM PMSF, 50 mM NaF, 200 mM sodium vanadate, 5 mg/ml aprotinin and 5 mg/ml leupeptin. Cell lysates were boiled for 5 min and electrophoresed on 15% SDS-PAGE and were then blotted with monoclonal IL-18 antibodies (R&D Systems, Minneapolis, Minn.). Blots were developed using horseradish peroxidase-conjugated secondary antibodies and the ECL detection system (Amersham Pharmacia Biotech).

RNA Extraction and IL-18 RT-PCR:

Total RNA was prepared from treated or non treated human keratinocytes by using Tri-reagent (Sigma Aldrich, Rehovot, Israel). Oligo(dt) primed cDNA was synthesized using 2 μg of total RNA. mRNA/cDNA specific cytokine primer pairs were designed and PCR was performed using the following primer pairs (5 μM each): IL-18 (product 558 bp): 178-201 [5'-ATGGCTGCTGAACCAGTAGAAGAC-3'], 735-759 [5'-CTAGTCTTCGTTTTGAACAGTGAAC-3']. Cycling conditions were 95° C., 4 minutes; 94° C., 1 minute, 65° C., 1 minute; and 72° C., 1 minute for 29 cycles. GPDH (glyceraldehyde-phosphate-dehydrogenase, product 500 bp) was used as a control: [5'-CACAGTCCATGCCATCACTG-3'],[5'-TACTCCTTGGAGGCCATGTG-3']. The amplified products were visualized using ethidium bromide staining.

Statistical Analysis:

Data are presented as mean±SE. For comparisons of means of the various groups, the pairwise t test was used. Survival curves were statistically analyzed by comparing the cumulative percentage of survival using the Gehan-Wilcoxon test.

Experimental Results

Inhibition of Caspase-1/IL-1-β-Converting Enzyme (ICE) by AS101 in a Concentration-dependent Manner:

AS101 was tested for its possible inhibitory activity towards a member of the cysteine protease family, caspase-1 (ICE-Interleukin-β-converting enzyme). The enzymatic reaction was carried out with caspase-1 specific colorimetric substrate, Ac-YVAD-pNA, and in the absence or the presence of AS101 at different concentrations. The enzyme activity was tested for 1 hour and measured at 405 nm.

As shown in FIG. 1, measurement of enzymatic activity, expressed as percent residual enzymatic activity, shows that AS101 inhibits ICE activity directly, in a concentration-dependant manner. 0 μM in the graph represents enzyme activity in the absence of AS101, as a positive control. Caspase-1 specific inhibitor (Ac-YVAD-CHO) was added at the concentration of 0.1 μM as an internal control for the assay (data not shown).

*$p<0.05$ decrease vs caspase-1(0), **$p<0.01$ decrease vs caspase-1 (0). Results represent means±SE of two experiments.

Inhibitory Effect of AS101 on the Extracellular Levels of SAC-induced Secretion of Active IL-18 and IL-1β by PMBC:

In order to determine whether AS101 is capable of inhibiting two ICE substrates, IL-18 and IL-1-β, SAC (*Staphylococcus aureus* Cowan strain) was used as a bacterial antigen which can stimulate PMBC to produce and secrete these two highly active inflammatory cytokines. PBMC ($2.5\times10^6$ cells/ml) were treated with various concentrations of AS101 and after 1 hour were stimulated with SAC ($10^{-3}$ V/V). Results represent means±SE of three experiments **$p<0.05$ decrease vs SAC; *$p<0.01$ decrease vs SAC. Optimal concentration of SAC for cytokine secretion stimulation was $10^{-3}$ v/v (data not shown).

Treatment with AS101 was shown to decrease SAC-induced secretion levels of IL-18 (FIG. 2*a*) and IL-1-β (FIG. 2B) after 24 hours, in a concentration dependent manner. The decrease in IL-18 and IL-β secretion is significant starting from 0.5 to 1 μg/ml ($p<0.05$) and 1.5 to 2 μg/ml ($p<0.01$).

Inhibitory Effect of AS101 on Intracellular Levels of LPS and PMA Induced Active Form of IL-18 in Human HaCat Keratinocytes:

IL-18 is constitutively produced by keratinocytes after treatment with LPS or PMA. In order to determine whether the inhibitory effect of AS101 on the formation of the active form of IL-18 is consistent and will repeat itself in another type of cell culture, Western Blot analysis of total cellular proteins from human HaCat keratinocytes was performed using anti-IL-18 antibodies. Concentrations of PMA (10 ng/ml) and LPS (50 ng/ml), were optimal for IL-18 production.

Cultured keratinocytes ($1\times10^6$ cells/ml) were preincubated for 2 hours with AS101 (1 μg/ml) and then treated with PMA or LPS. Expression of IL-18 was assessed by WB analysis while α-tubulin was used as internal control. Each line was loaded with 30 μg of total proteins from human keratinocytes that were either untreated (control) or treated with PMA (FIG. 3*a*) or LPS (FIG. 3*b*) and treated with AS101 (FIG. 3*c*).

The results show that pretreatment of keratinocytes with AS101 (1 μg/ml) using optimal concentrations of PMA and LPS, produced a decrease in the amounts of the active form of IL-18. These data are representative of three different experiments.

Effect of AS101 on mRNA Levels of IL-18 in HaCat Cells:

In order to establish whether inhibition of IL-18 production is exerted at the transcriptional or post-transcriptional level, the effect of AS101 on mRNA IL-18 levels was examined, under experimental conditions similar to those of the previous experiment.

Changes at the IL-18 mRNA level were studied when keratinocytes were pretreated with AS101 (1 μg/ml) using optimal concentrations of PMA (10 ng/ml) and LPS (50 ng/ml). Total RNA was isolated from whole cell lysates. GAPDH was used as internal control. Cultured keratinocytes ($1\times10^6$ cells/ml) were either untreated (line 1) or treated with PMA at 5 ng/ml and 10 ng/ml (line 2 and 3 respectively) and with LPS at 40 ng/ml and 50 ng/ml (line 4 and 5 respectively).

Figure 4A:
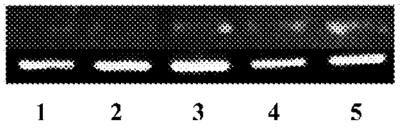
FIGS. 4*a-b* present Western Blot analysis of the induction of IL-18 by PMA (FIG. 4*a*) and LPS (FIG. 4*b*) at mRNA level.
Figure 4B:
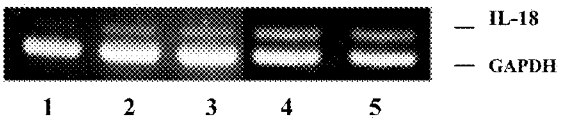

The concentration dependent induction of IL-18 by PMA or LPS at the mRNA level is shown in FIG. 4*a*. FIG. 4*b* shows cultured keratinocytes either untreated (line 1) or treated with PMA (10 ng/ml) (line 2) or with LPS (50 ng/ml) (line 4) or pre-incubated for 2 hours with AS101 (1 μg/ml) and then treated with PMA (10 ng/ml) (line 3) and LPS (50 ng/ml) (line 5) respectively. PCR products were amplified for 29 cycles. Changes in mRNA levels were not detected whether pretreated or not with AS101 (FIG. 4*b*). These results confirm that AS101 inhibits IL-18 on a post-transcriptional level. The results show one representative experiment out of two performed.

Role of Nitric Oxide in the Ability of AS101 to Inhibit Caspase-1 Activity and Release Mature IL-18:

In order to examine whether the elimination of NO will abrogate AS101 activity of IL-18 inhibition, the effect of nitric oxide synthase inhibitor (L-NAME), was studied.

L-NAME/D-NAME (20 nM) were delivered to PBMC ($2.5\times10^6$ cells/ml)$_2$ hours before AS101 (0.5 μg/ml). SAC ($10^{-3}$ v/v) was added 1 hour following AS101. Supernatants were collected after 24 hours and evaluated for IL-18 levels.

Figure 5:
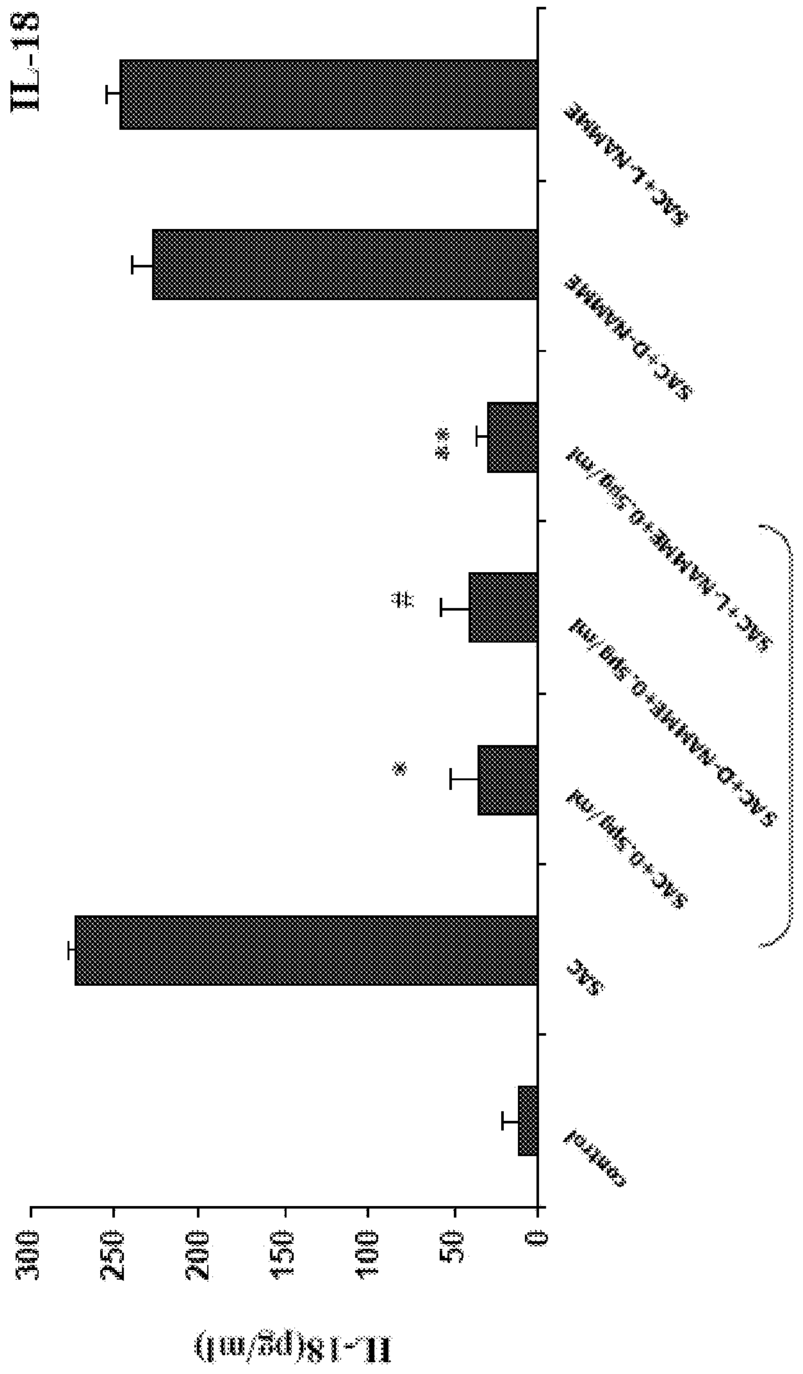
FIG. 5 is a bar graph demonstrating the role of nitric oxide in the ability of AS101 to inhibit caspase-1 activity.

FIG. 5 shows that the inhibitory effect of AS101 was not diminished after using L-NAME.

Results represent means±SE of three experiments in vitro. *$p<0.01$ decrease vs SAC. #$p<0.01$ decrease vs SAC+D-NAME. **$p<0.01$ decrease vs SAC+L-NAME.

Role of IFN-γ in the Ability of AS101 to Inhibit Caspase-1 Activity and Release Mature IL-18:

In order to investigate the possibility that enhancement of IFN-γ levels by AS101 might have a synergistic effect on IL-18 inhibition, rhIFN-γ neutralizing antibody (0.1 μg/ml) was delivered to PBMC ($2.5\times10^6$ cells/ml) 2 hours before AS101 (0.5 μg/ml). SAC ($10^{-3}$ v/v) was added 1 hour following AS101. Supernatants were collected after 24 hours and evaluated for IL-18 levels.

Figure 6:
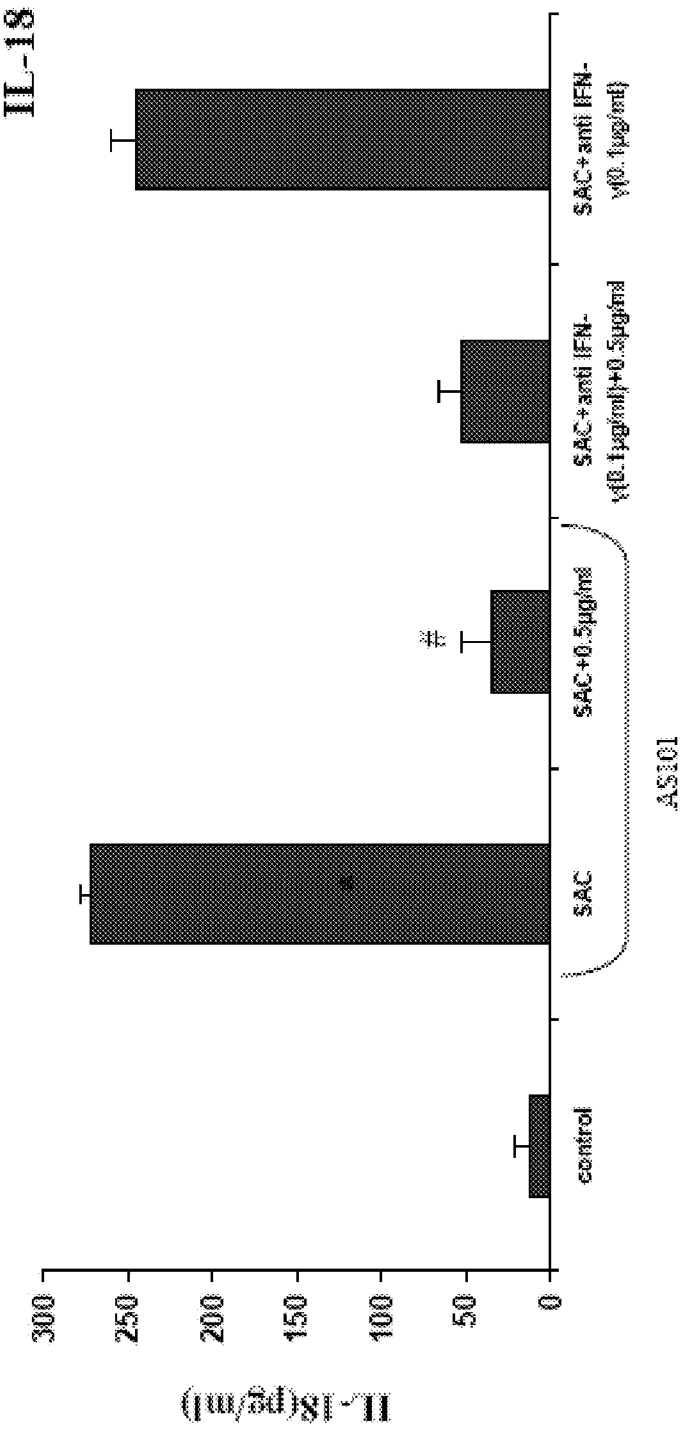
FIG. 6 is a bar graph demonstrating the role of IFN-γ in the ability of AS101 to inhibit caspase-1 activity.

As shown in FIG. 6, neutralization of IFN-γ by using anti IFN-γ neutralizing antibodies does not abrogate IL-18 inhibition.

Results represent means±SE of three experiments in vitro. *$p<0.01$ decrease vs SAC. #$p<0.01$ decrease vs SAC+IFN-γ neutr Ab.

Plasma Levels of IL-18 and IL-1β in AS101-treated Mice Following Induction of Sepsis:

PBS (control) and AS101 at various concentrations were injected into c57BL/6J mice 2 hours following induction of sepsis by LPS (0.5 mg/mouse) treatment. 24 hours after LPS injection, mice were sacrificed and evaluated for plasma concentration of these cytokines in order to determine whether AS101 can inhibit production of IL-18 and IL-1β in vivo.

Figure 7A:
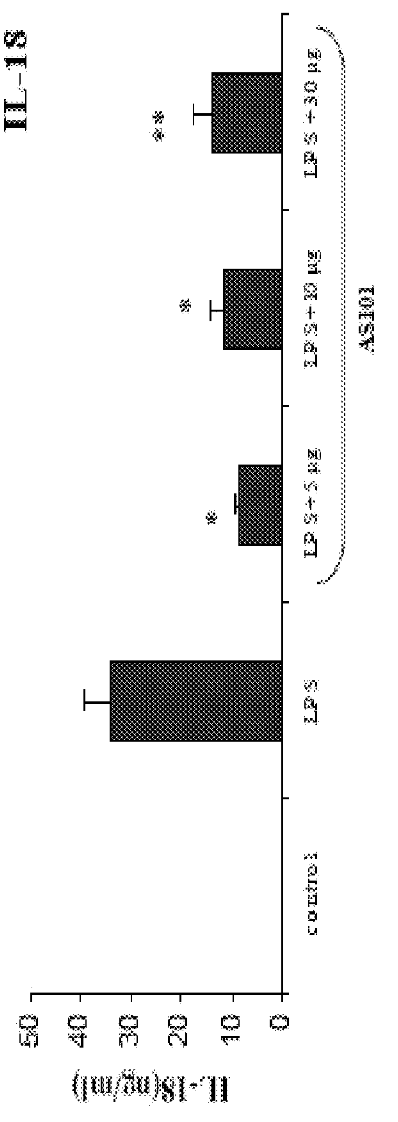
FIGS. 7*a-b* are bar graphs demonstrating the effect of AS101 on serum levels of IL-18 (FIG. 7*a*) and IL-1β (FIG. 7*b*) in LPS-induced septic mice.
Figure 7B:
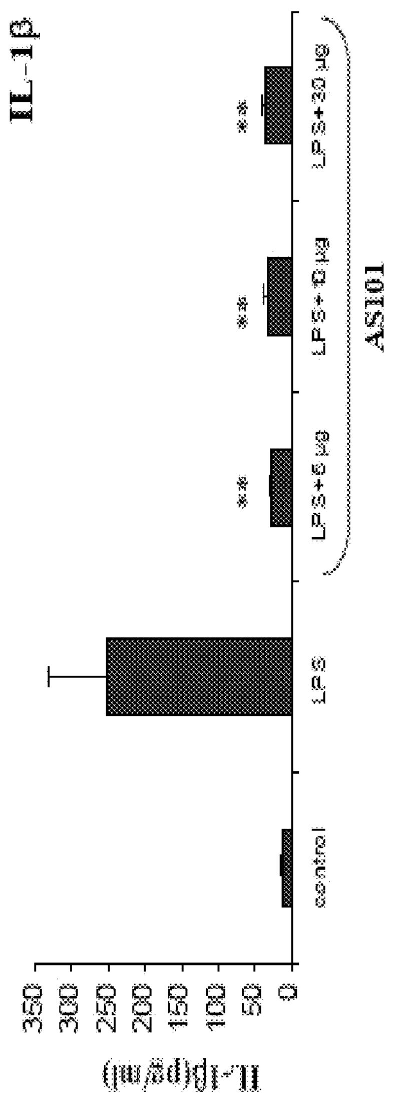

As shown in FIG. 7, at concentration of 5 μg/mouse and 10 μg/mouse, AS101 significantly inhibited levels of these cytokines.

Results represent a total of 6 mice/group. **$p<0.05$ decrease vs LPS, *$p<0.01$ decrease vs LPS.

Enhanced Survival of AS101-treated Mice Following Induction of Sepsis:

In order to study the relationship between the above in vitro and in vivo results and the effect of AS101 on survival of mice following induction of sepsis, AS101 at a concentration of 10 μg/mouse was injected into LPS-induced septic mice at various time points after LPS (0.35 mg/mouse) treatment. Survival was monitored for 9 days.

Figure 8:
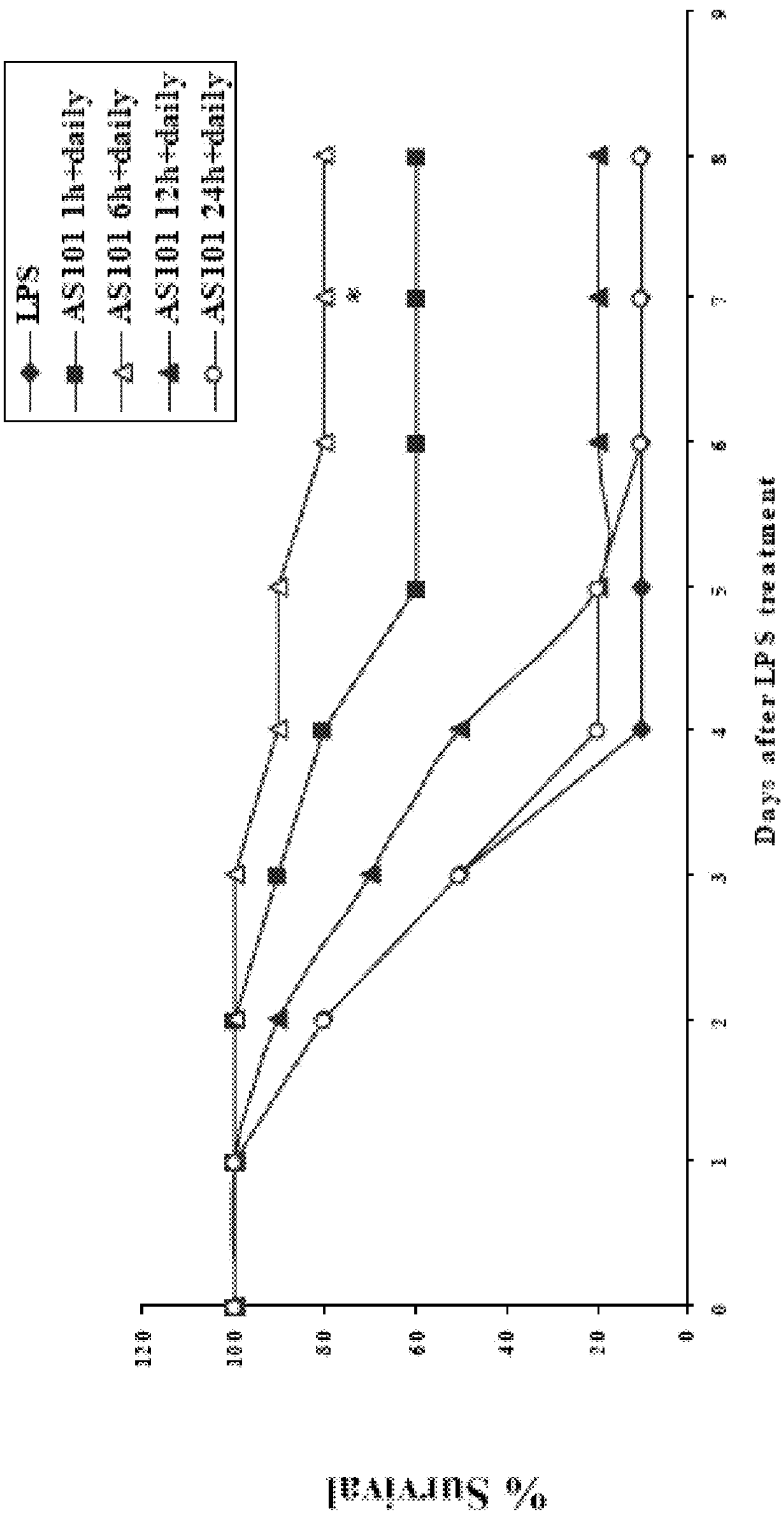
FIG. 8 is a plot demonstrating the effect of AS101 on survival of LPS-induced septic mice.

As shown in FIG. 8, it was found that treatment with AS101 had a beneficial effect when injected after sepsis induction, in comparison with AS101 treatment 24 hours before sepsis induction (data not shown). The optimal dose of AS101 was 10 μg/mouse, injected 6 hours following LPS and thereafter every day until the end of the experiment.

Results shown represent a total of 10 mice/group.*$p<0.05$ increase vs LPS.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating a condition in which inhibition of interleukin-1β-converting enzyme is beneficial, the method comprising administering to a subject in need thereof a therapeutically effective amount of at least one tellurium-containing compound selected from the group consisting of tellurium dioxide ($TeO_2$), a complex of $TeO_2$, a compound having general Formula I:

Formula I

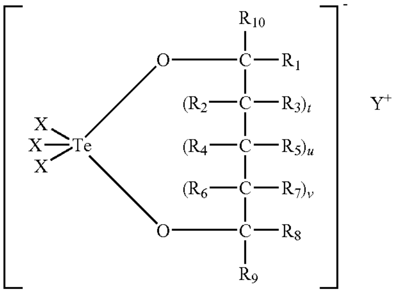

a compound having general Formula II:

Formula II

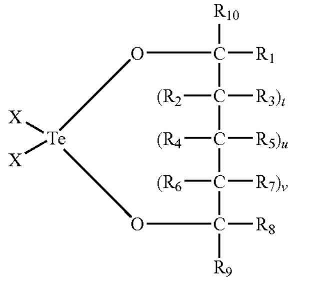

and a compound having general Formula III:

Formula III

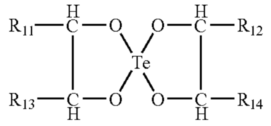

wherein:

each of t, u and v is independently 0 or 1;

Y is selected from the group consisting of ammonium, phosphonium, potassium, sodium and lithium;

X is a halogen atom; and each of $R_1$-$R_{14}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, carboxyalkyl, acyl, amide, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido, and the condition in which inhibition of interleukin-1β-converting enzyme is beneficial is selected from the group consisting of an excess dietary alcohol intake disease, uveitis, inflammatory peritonitis, osteoarthritis, pancreatitis, asthma, adult respiratory distress syndrome, glomerulonephritis, rheumatoid arthritis, scleroderma, chronic thyroiditis, Grave's disease, autoimmune hemolytic anemia, autoimmune neutropenia, thrombocytopenia, chronic active hepatitis, myasthenia gravis, inflammatory bowel disease, Crohn's disease, atopic dermatitis, scarring, graft vs host disease, organ transplant rejection, organ apoptosis after burn injury, osteoporosis, leukemia or a related disorder, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, septic shock, a burn, Shigellosis, Huntington's disease, Kennedy's disease, prion disease, cerebral ischemia, epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, neurological damage due to stroke, ulcerative colitis, hepatitis-B, hepatitis-C, hepatitis-G, yellow fever, dengue fever, Japanese encephalitis, renal disease, polycystic kidney disease, HIV infection, tuberculosis, any of various forms of cancer, organ failure, and meningitis.

2. The method of claim 1, wherein said tellurium-containing compound has said general Formula I.

3. The method of claim 2, wherein t, u and v are each 0.

4. The method of claim 3, wherein each of $R_1$, $R_8$, $R_9$ and $R_{10}$ is hydrogen.

5. The method of claim 4, wherein X is a halogen atom.

6. The method of claim 5, wherein X is chloro.

7. The method of claim 6, wherein Y is ammonium.

8. The method of claim 1, wherein said tellurium-containing compound is ammonium trichloro(dioxyethylene-O,O') tellurate.

9. The method of claim 1, wherein said condition is selected from the group consisting of an excess dietary alcohol intake disease, uveitis, inflammatory peritonitis, osteoarthritis, pancreatitis, asthma, adult respiratory distress syndrome, glomerulonephritis, rheumatoid arthritis, scleroderma, chronic thyroiditis, Grave's disease, autoimmune hemolytic anemia, autoimmune neutropenia, thrombocytopenia, chronic active hepatitis, myasthenia gravis, inflammatory bowel disease, Crohn's disease, atopic dermatitis, scarring, graft vs host disease, organ transplant rejection, organ apoptosis after burn injury, osteoporosis, haemorrhagic shock, sepsis, septic shock, a burn, Shigellosis, myocardial ischemia, acute and chronic heart disease, myocardial infarction, congestive heart failure, atherosclerosis, coronary artery bypass graft, multiple sclerosis, HIV-related encephalitis, aging, ulcerative colitis, hepatitis-B, hepatitis-C, hepatitis-G, yellow fever, dengue fever, Japanese encephalitis, renal disease, polycystic kidney disease, HIV infection, tuberculosis, organ failure, and meningitis.

10. The method of claim 1, wherein said therapeutically effective amount ranges from about 0.01 $mg/m^2/day$ to about 20 $mg/m^2/day$.

11. The method of claim 1, wherein said at least one tellurium-containing compound forms a part of a pharmaceutical composition, said pharmaceutical composition further comprising a pharmaceutically acceptable carrier.

12. The method of claim 11, wherein the concentration of said at least one tellurium-containing compound ranges from about 0.01 weight percent to about 50 weight percent of the total weight of said composition.

13. The method of claim 12, wherein the concentration of said at least one tellurium-containing compound ranges from about 0.1 weight percent to about 25 weight percent of the total weight of said composition.

14. The method of claim 11, wherein said pharmaceutical composition further comprises at least one additional active agent, the at least one additional active agent comprising one or more of an antibiotic agent. an antimicrobial agent, an antibacterial agent, an antifungal agent, an antiviral agent, a steroidal anti-inflammatory agent, a non-steroidal anti-inflammatory agent, an anesthetic agent, an antipruriginous agent, an antiprotozoal agent, an antioxidant, an antineoplastic agent, an immunomodulator, an interferon, an antidepressant, an antihistamine, a vitamin, and a hormone.

15. The method of claim 9, wherein said tellurium-containing compound is ammonium trichloro(dioxyethylene-O,O') tellurate.

16. The method of claim 9, wherein said condition is selected from the group consisting of haemorrhagic shock, sepsis, septic shock, a burn, Shigellosis, myocardial ischemia, acute or chronic heart disease, myocardial infarction, congestive heart failure, atherosclerosis, coronary artery bypass graft, multiple sclerosis, HIV-related encephalitis, aging, ulcerative colitis, hepatitis-B, hepatitis-C, hepatitis-G, yellow fever, dengue fever, Japanese encephalitis, and polycystic kidney disease.

17. The method of claim 16, wherein said tellurium-containing compound is ammonium trichloro(dioxyethylene-O,O')tellurate.

18. The method of claim 16, wherein said condition is selected from the group consisting of haemorrhagic shock, sepsis, septic shock, a burn, myocardial ischemia, acute and chronic heart disease, myocardial infarction, congestive heart failure, atherosclerosis, coronary artery bypass graft, multiple sclerosis, aging, renal disease, and polycystic kidney disease.

19. The method of claim 18, wherein said tellurium-containing compound is ammonium trichloro(dioxyethylene-O,O')tellurate.

20. The method of claim 18, wherein said condition is selected from the group consisting of sepsis and septic shock.

21. The method of claim 20, wherein said tellurium-containing compound is ammonium trichloro(dioxyethylene-O,O')tellurate.

* * * * *